US008333953B2

(12) United States Patent
Lu et al.

(10) Patent No.: US 8,333,953 B2
(45) Date of Patent: Dec. 18, 2012

(54) METHODS OF DELIVERY OF EXOGENOUS PROTEINS TO THE CYTOSOL AND USES THEREOF

(75) Inventors: Yichen Lu, Wellesley, MA (US); Huyen Cao, San Francisco, CA (US)

(73) Assignees: The General Hospital Corporation, Boston, MA (US); President and Fellows of Harvard College, Boston, MA (US)

( * ) Notice: Subject to any disclaimer, the term of this patent is extended or adjusted under 35 U.S.C. 154(b) by 97 days.

(21) Appl. No.: 12/782,659

(22) Filed: May 18, 2010

(65) Prior Publication Data

US 2010/0311105 A1 Dec. 9, 2010

Related U.S. Application Data

(62) Division of application No. 10/473,190, filed as application No. PCT/US02/09680 on Mar. 28, 2002, now Pat. No. 7,754,219.

(60) Provisional application No. 60/279,366, filed on Mar. 28, 2001.

(51) Int. Cl.
*A61K 49/00* (2006.01)
*A61K 39/00* (2006.01)
*A61K 39/04* (2006.01)

(52) U.S. Cl. .... 424/9.1; 424/9.2; 424/185.1; 424/190.1; 424/192.1; 424/234.1; 424/248.1

(58) Field of Classification Search .................. 424/9.1, 424/9.2, 185.1, 190.1, 192.1, 234.1, 248.1
See application file for complete search history.

(56) References Cited

U.S. PATENT DOCUMENTS

| 5,677,274 | A | 10/1997 | Leppla et al. |
| 6,592,872 | B1 | 7/2003 | Klimpel et al. |
| 2003/0190332 | A1 | 10/2003 | Gilad et al. |

FOREIGN PATENT DOCUMENTS

| WO | 94/18332 A2 | 8/1994 |
| WO | 97/23236 | 7/1997 |

OTHER PUBLICATIONS

Anderson, K. S. et al., Journal of Immunology. 151:3407-19 (1993).
Androlewicz, M. J. et al., Proc. Natl. Acad. Sci. USA, 90:9130-4 (1993).
Ballard, J. D., et al., Infection & Immunity. 66:615-9 (1998).
Borrow, P. et al., J. Virol. 68:6103-6110 (1994).
Borrow, P. et al., Nature Medicine. 3:205-211 (1997).
Brodie et al., Nat. Med. 5:34-41 (1999).
Cao, H. et al., J. Virol. 71:8615-23 (1997).
Cao, H. et al., J. Infec Dis. 182:1350-56 (2000).
Cao, H. et al., J. Infect. Dis. 185: 244-51 (2002).
Doling, A. et al., Infection & Immunity. 67: 90-6 (1999).
Falk, K. et al., J. Exp. Med. 174:425-434 (1991).
Finbloom, D. S. et al. Clinical & Experimental Immunology. 67:205-10 (1987).
Geisow, M. J. et al., Journal of Cell Biology. 80-645-52 (1981).
Goldberg, A. L. et al., Nature. 357:375-9 (1992).
Hanna, P. C. et al., Proc. Nat Acad, Sci. USA. 90:10198-201 (1993).
Letvin, Science 280:1875-80 (1998).
Ogg, C.S. et al., Science 279:2103-6 (1998).
Schmitz, J. et al. Science 283:857-60 (1999).
Arora, Naveen; Molecular and Cellular Biochemistry; 177(1-2):7-14 (1997).
Barth, H. et al.; Infection and Immunity; 66(4):1364-1369 (1998).
Falnes, Pal O. et al.; Current Opinion in Cell Biology; 12(4):407-413 (2000).
Guidi-Rontani, Chantal et al.; Cellular Microbiology; 2(3):259-264 (2000).
Gupta, Pankaj, et al.; Biochemical and Biophysical Research Communications; 280(1):158-163 (2001).
Kushner, Nicholas at al.; PNAS; 100(11):6652-6657 (2003).
Stenmark, Harald et al.; The Journal of Cell Biology; 113(5):1025-11032 (1991).
Goletz et al., Proceedings of the National Academy of Sciences, USA, vol. 94 No. 22, pp. 12059-12064 (Oct. 1997).
Bowie at al., "Deciphering the Message in Protein Sequences: Tolerance to Amino Acid Substitutions;" Science, vol. 247 No. 4948, pp. 1306-1310 (Mar. 1990).
Bragg and Robertson, "Nucleotide sequence and analysis of the lethal factor gene (lef) from *Bacillus anthracis*," Gene, vol. 81 No. 1, pp. 45-54 (Sep. 1989).
Fayolle at al., "In vivo induction of CTL responses by recombinant adenylate cyclase of *Bordetella pertussis* carrying viral CD8+ T cell epitopes," Journal of Immunology, vol. 156 No. 12, pp. 4697-4706 (Jun. 1996).
Robertson et al., "Molecular Cloning and expression in *Escherichia coli* of the lethal factors gene of *Bacillus antracis*," Gene, vol. 44, No. 1, pp. 71-78 (1986).
Score Search Results, SEQ ID No. 2—alignment of result 1.
Robinson et al., "Lymphocyte Stimulation by Phytohemagglutinin and Tumor Cells of Malignant Effusions," Cancer Research, vol. 34, pp. 1548-1551, Jul. 1974.
Arora, Naveen et al., The Journal of Biological Chemistry, vol. 268 (No. 5), p. 3334-3341, (Feb. 15, 1993).
Arora, Naveen et al., The Journal of Biological Chemistry, vol. 269 (No. 42), p. 26165-26171, (Oct. 21 1994).
Figueiredo, Dayse et al., Infection and Immunity, vol. 63 (No. 8), p. 3218-3221, (Aug. 1995).
Leppla, S.H. et al., Journal of Applied Microbiology, 87:284, (1999).
Tang, Guangoing et al., Infection and Immunity, vol. 67 (No. 6), p. 3055-3060, (Jun. 1999).
Lu, Yichen et al., PNAS, vol. 97 (No. 14), p. 8027-8032, (Jul. 5, 2000).

*Primary Examiner* — Rodney P. Swartz
(74) *Attorney, Agent, or Firm* — Nixon Peabody LLP; Ronald I. Eisenstein

(57) ABSTRACT

The present invention is directed to a method for delivering exogenous proteins to the cytosol, by binding a target antigen (such as a protein) to a transport factor that contains a fragment of a bipartite protein exotoxin, but not the corresponding protective antigen. Preferably, the target antigen is fused to the transport factor. Preferred transport factors include the protective antigen binding domain of lethal factor (LFn) from *B. anthracis*, consisting of amino acids 1-255, preferably a fragment of at least 80 amino acids that shows at least 80% homology to LFn, and a fragment of about 105 amino acids from the carboxy portion that does not bind PA. The target antigen can include any molecule for which it would be desirable to elicit a CMI response, including viral antigens and tumor antigens.

19 Claims, 28 Drawing Sheets

LF

```
  1 mnikkefikv ismsclvtai tlsgpvfipl vqgagghgdv gmhvkekekn kdenkrkdee
 61 rnktqeehlk eimkhivkie vkgeeavkke aaekllekvp sdvlemykai ggkiyivdgd
121 itkhisleal sedkkkikdi ygkdallheh yvyakegyep vlviqssedy ventekalnv
181 yyeigkilsr dilskinqpy qkfldvlnti knasdsdgqd llftnqlkeh ptdfsvefle
241 qnsnevqevf akafayyiep qhrdvlqlya peafnymdkf neqeinlsle elkdqrmlsr
301 yekwekikqh yqhwsdslse egrgllkklq ipiepkkddi ihslsqeeke llkriqidss
361 dflsteekef lkklqidird slseeekell nriqvdssnp lsekekeflk klkldiqpyd
421 inqrlqdtgg lidspsinld vrkqykrdiq nidallhqsi gstlynkiyl yenmninnlt
481 atlgadlvds tdntkinrgi fnefkknfky sissnymivd inerpaldne rlkwriqlsp
541 dtragyleng klilqrnigl eikdvqiikq sekeyirida kvvpkskidt kiqeaqlnin
601 qewnkalglp kytklitfnv hnryasnive saylilnewk nniqsdlikk vtnylvdgng
661 rfvftditlp niaeqythqd eiyeqvhskg lyvpesrsil lhgpskgvel rndsegfihe
721 fghavddyag ylldknqsdl vtnskkfidi fkeegsnlts ygrtneaeff aeafrlmhst
781 dhaerlkvqk napktfqfin dqikfiins
```

*FIG. 2A*

LFn

```
  1 mnikkefikv ismsclvtai tlsgpvfipl vqgagghgdv gmhvkekekn kdenkrkdee
 61 rnktqeehlk eimkhivkie vkgeeavkke aaekllekvp sdvlemykai ggkiyivdgd
121 itkhisleal sedkkkikdi ygkdallheh yvyakegyep vlviqssedy ventekalnv
181 yyeigkilsr dilskinqpy qkfldvlnti knasdsdgqd llftnqlkeh ptdfsvefle
241 qnsnevqevf akafayyiepqhrdvlqlya peafnymdkf neqeinlsl
```

*FIG. 2B*

Fragment 3

```
gkilsr dilskinqpy qkfldvlnti knasdsdgqd llftnqlkeh ptdfsvefle qnsnevqevf
akafayyiep qhrdvlqlya peafnymdkf neqeinls
```

*FIG. 2C*

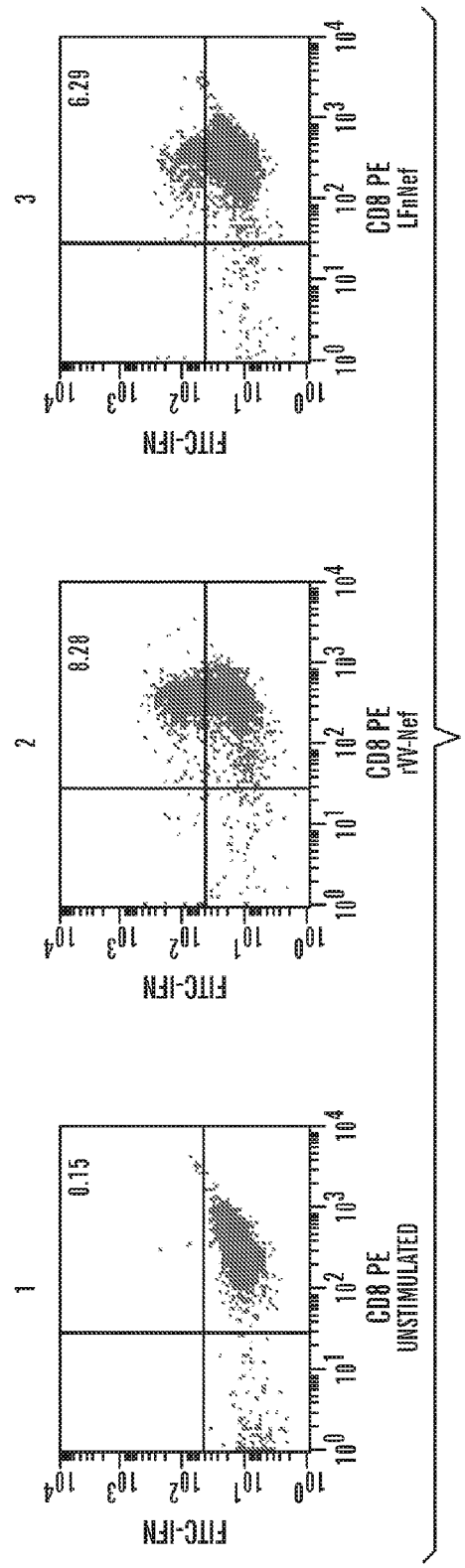
FIG. 7A NEF-SPECIFIC CTL
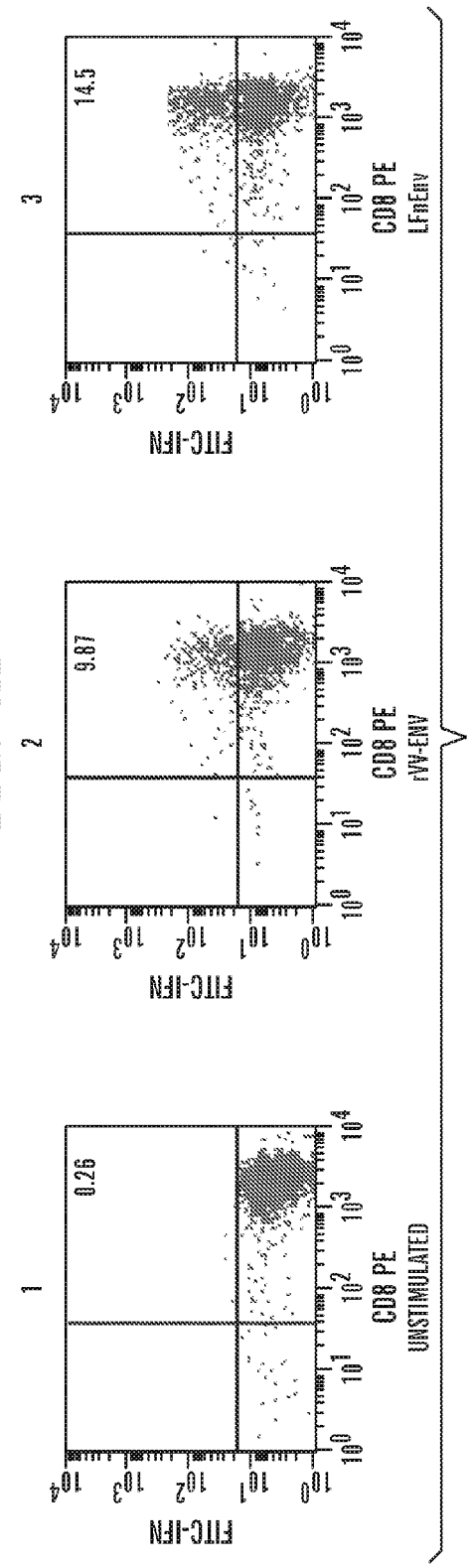
FIG. 7B ENV-SPECIFIC CTL

LN-GFP @37 C for 1 hr

LN-GFP @37 C for 1 hr

LN-GFP @37 C for 1 hr

LN-GFP @37 C for 1 hr

LN-GFP @37 C for 1 hr

LN-GFP @37 C for 1 hr

LN-GFP @37 C for 1 hr

LN-GFP @37 C for 1 hr

LN-GFP @37 C for 1 hr

LN-GFP @37 C for 1 hr

LN-GFP @37 C for 1 hr

LN-GFP @37 C for 1 hr

Transferin

Merge

Merge

Merge

Lamp-2

Lamp-2

Lamp-2

Lamp-2

LN-GFP

LN-GFP

LN-GFP

LN-GFP

Merge

Merge

Merge

Merge

EEA-1

EEA-1

EEA-1

EEA-1

LN-GFP

LN-GFP

LN-GFP

LN-GFP

Merge

Merge

Merge

Merge

Golgi

Golgi

LN-GFP

LN-GFP

Merge

Merge

HeLa cells were incubated with 40 µg/ml
LNgfp for 2h @37 C, then fixed and
stained with anti-20s preteasome
polyclonal antibody (CalBiochem).

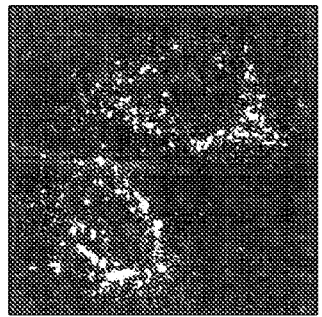

LNgfp
*FIG. 15A*

HeLa cells were incubated with 40 µg/ml
LNgfp for 2h @37 C, then fixed and
stained with anti-20s preteasome
polyclonal antibody (CalBiochem).

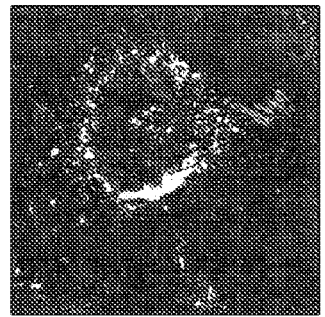

LNgfp
*FIG. 15B*

HeLa cells were incubated with 40 µg/ml
LNgfp for 2h @37 C, then fixed and
stained with anti-20s preteasome
polyclonal antibody (CalBiochem).

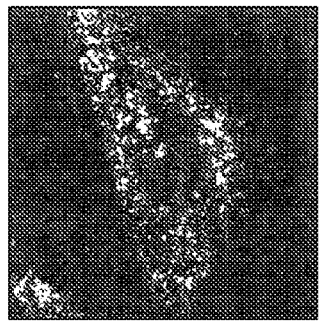

LNgfp
*FIG. 15C*

HeLa cells were incubated with 40 µg/ml
LNgfp for 2h @37 C, then fixed and
stained with anti-20s preteasome
polyclonal antibody (CalBiochem).

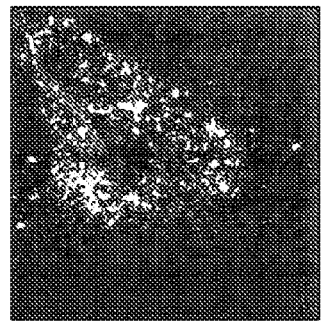

LNgfp
*FIG. 15D*

HeLa cells were incubated with 40 µg/ml
LNgfp for 2h @37 C, then fixed and
stained with anti-20s preteasome
polyclonal antibody (CalBiochem).

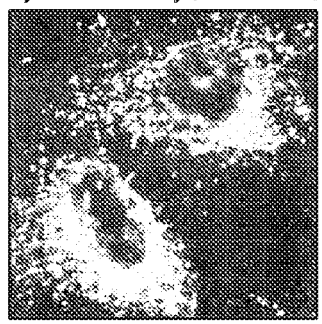

20S
*FIG. 15E*

HeLa cells were incubated with 40 µg/ml
LNgfp for 2h @37 C, then fixed and
stained with anti-20s preteasome
polyclonal antibody (CalBiochem).

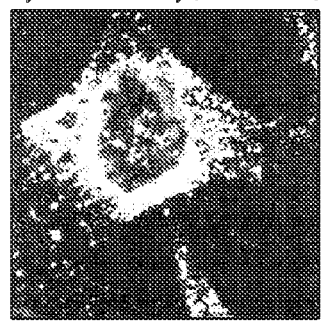

20S
*FIG. 15F*

HeLa cells were incubated with 40 μg/ml
LNgfp for 2h @37 C, then fixed and
stained with anti-20s preteasome
polyclonal antibody (CalBiochem).

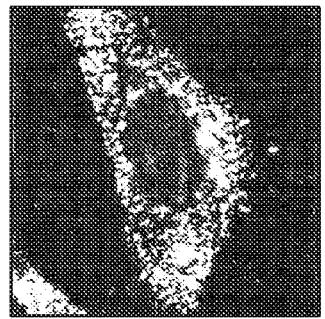

20S
*FIG. 15G*

HeLa cells were incubated with 40 μg/ml
LNgfp for 2h @37 C, then fixed and
stained with anti-20s preteasome
polyclonal antibody (CalBiochem).

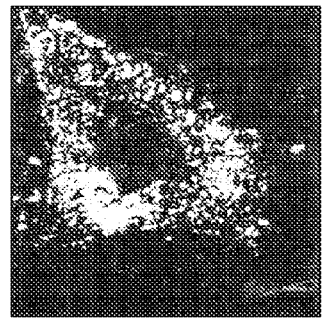

20S
*FIG. 15H*

HeLa cells were incubated with 40 μg/ml
LNgfp for 2h @37 C, then fixed and
stained with anti-20s preteasome
polyclonal antibody (CalBiochem).

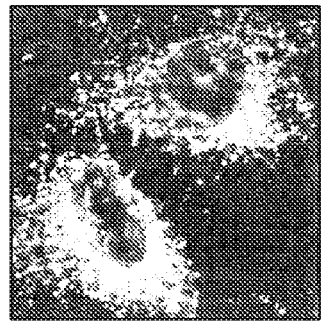

Merge
*FIG. 15I*

HeLa cells were incubated with 40 μg/ml
LNgfp for 2h @37 C, then fixed and
stained with anti-20s preteasome
polyclonal antibody (CalBiochem).

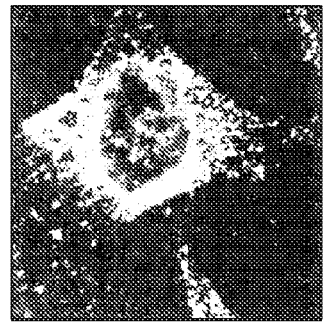

Merge
*FIG. 15J*

HeLa cells were incubated with 40 μg/ml
LNgfp for 2h @37 C, then fixed and
stained with anti-20s preteasome
polyclonal antibody (CalBiochem).

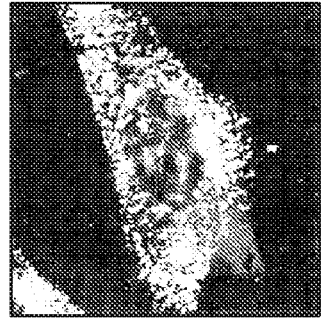

Merge
*FIG. 15K*

HeLa cells were incubated with 40 μg/ml
LNgfp for 2h @37 C, then fixed and
stained with anti-20s preteasome
polyclonal antibody (CalBiochem).

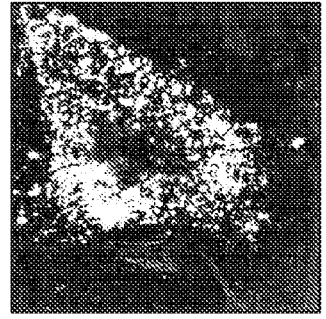

Merge
*FIG. 15L*

SEQUENCE LISTING

<160> NUMBER OF SEQ ID NOS: 6

<210> SEQ ID NO 1
<211> LENGTH: 809
<212> TYPE: PRT
<213> ORGANISM: Bacillus anthracis

<400> SEQUENCE: 1

Met Asn Ile Lys Lys Glu Phe Ile Lys Val Ile Ser Met Ser Cys Leu
 1               5                  10                  15

Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Glu Arg Asn Lys Thr
    50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys

```
                         165                 170                 175
Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
            195                 200                 205

Thr Ile Lys Asn Ala Ser Asp Ser Asp Gly Gln Asp Leu Leu Phe Thr
            210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
            245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
            275                 280                 285

Leu Glu Glu Leu Lys Asp Gln Arg Met Leu Ser Arg Tyr Glu Lys Trp
            290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
            325                 330                 335

Lys Asp Asp Ile Ile His Ser Leu Ser Gln Glu Glu Lys Glu Leu Leu
            340                 345                 350

Lys Arg Ile Gln Ile Asp Ser Ser Asp Phe Leu Ser Thr Glu Glu Lys
            355                 360                 365

Glu Phe Leu Lys Lys Leu Gln Ile Asp Ile Arg Asp Ser Leu Ser Glu
            370                 375                 380

Glu Glu Lys Glu Leu Leu Asn Arg Ile Gln Val Asp Ser Ser Asn Pro
385                 390                 395                 400

Leu Ser Glu Lys Glu Lys Glu Phe Leu Lys Lys Leu Lys Leu Asp Ile
            405                 410                 415

Gln Pro Tyr Asp Ile Asn Gln Arg Leu Gln Asp Thr Gly Gly Leu Ile
            420                 425                 430

Asp Ser Pro Ser Ile Asn Leu Asp Val Arg Lys Gln Tyr Lys Arg Asp
            435                 440                 445

Ile Gln Asn Ile Asp Ala Leu Leu His Gln Ser Ile Gly Ser Thr Leu
            450                 455                 460

Tyr Asn Lys Ile Tyr Leu Tyr Glu Asn Met Asn Ile Asn Asn Leu Thr
465                 470                 475                 480

Ala Thr Leu Gly Ala Asp Leu Val Asp Ser Thr Asp Asn Thr Lys Ile
            485                 490                 495

Asn Arg Gly Ile Phe Asn Glu Phe Lys Lys Asn Phe Lys Tyr Ser Ile
            500                 505                 510

Ser Ser Asn Tyr Met Ile Val Asp Ile Asn Glu Arg Pro Ala Leu Asp
            515                 520                 525

Asn Glu Arg Leu Lys Trp Arg Ile Gln Leu Ser Pro Asp Thr Arg Ala
530                 535                 540

Gly Tyr Leu Glu Asn Gly Lys Leu Ile Leu Gln Arg Asn Ile Gly Leu
545                 550                 555                 560

Glu Ile Lys Asp Val Gln Ile Ile Lys Gln Ser Glu Lys Glu Tyr Ile
            565                 570                 575

Arg Ile Asp Ala Lys Val Val Pro Lys Ser Lys Ile Asp Thr Lys Ile
            580                 585                 590
```

```
Gln Glu Ala Gln Leu Asn Ile Asn Gln Glu Trp Asn Lys Ala Leu Gly
            595                 600                 605

Leu Pro Lys Tyr Thr Lys Leu Ile Thr Phe Asn Val His Asn Arg Tyr
610                 615                 620

Ala Ser Asn Ile Val Glu Ser Ala Tyr Leu Ile Leu Asn Glu Trp Lys
625                 630                 635                 640

Asn Asn Ile Gln Ser Asp Leu Ile Lys Lys Val Thr Asn Tyr Leu Val
            645                 650                 655

Asp Gly Asn Gly Arg Phe Val Phe Thr Asp Ile Thr Leu Pro Asn Ile
            660                 665                 670

Ala Glu Gln Tyr Thr His Gln Asp Glu Ile Tyr Glu Gln Val His Ser
            675                 680                 685

Lys Gly Leu Tyr Val Pro Glu Ser Arg Ser Ile Leu Leu His Gly Pro
690                 695                 700

Ser Lys Gly Val Glu Leu Arg Asn Asp Ser Glu Gly Phe Ile His Glu
705                 710                 715                 720

Phe Gly His Ala Val Asp Asp Tyr Ala Gly Tyr Leu Leu Asp Lys Asn
            725                 730                 735

Gln Ser Asp Leu Val Thr Asn Ser Lys Lys Phe Ile Asp Ile Phe Lys
            740                 745                 750

Glu Glu Gly Ser Asn Leu Thr Ser Tyr Gly Arg Thr Asn Glu Ala Glu
            755                 760                 765

Phe Phe Ala Glu Ala Phe Arg Leu Met His Ser Thr Asp His Ala Glu
770                 775                 780

Arg Leu Lys Val Gln Lys Asn Ala Pro Lys Thr Phe Gln Phe Ile Asn
785                 790                 795                 800

Asp Gln Ile Lys Phe Ile Ile Asn Ser
            805

<210> SEQ ID NO 2
<211> LENGTH: 289
<212> TYPE: PRT
<213> ORGANISM: Bacillus anthracis

<400> SEQUENCE: 2

Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Glu Arg Asn Lys Thr
    50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Glu Lys Leu Leu
                85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160
```

```
Val Leu Val Ile Gln Ser Ser Glu Asp Tyr Val Glu Asn Thr Glu Lys
            165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
            195                 200                 205

Thr Ile Lys Asn Ala Ser Asp Ser Asp Gly Gln Asp Leu Leu Phe Thr
            210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
            245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
            275                 280                 285

Leu

<210> SEQ ID NO 3
<211> LENGTH: 104
<212> TYPE: PRT
<213> ORGANISM: Bacillus anthracis

<400> SEQUENCE: 3

Gly Lys Ile Leu Ser Arg Asp Ile Leu Ser Lys Ile Asn Gln Pro Tyr
1               5                   10                  15

Gln Lys Phe Leu Asp Val Leu Asn Thr Ile Lys Asn Ala Ser Asp Ser
            20                  25                  30

Asp Gly Gln Asp Leu Leu Phe Thr Asn Gln Leu Lys Glu His Pro Thr
        35                  40                  45

Asp Phe Ser Val Glu Phe Leu Glu Gln Asn Ser Asn Glu Val Gln Glu
    50                  55                  60

Val Phe Ala Lys Ala Phe Ala Tyr Tyr Ile Glu Pro Gln His Arg Asp
65                  70                  75                  80

Val Leu Gln Leu Tyr Ala Pro Glu Ala Phe Asn Tyr Met Asp Lys Phe
                85                  90                  95

Asn Glu Gln Glu Ile Asn Leu Ser
            100

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Arg Phe Tyr Lys Thr Leu Arg Ala
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

```
Lys Glu Lys Gly Gly Leu Glu Gly Leu
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Glu Asn Leu Trp Val Thr Val Tyr
  1               5
```

METHODS OF DELIVERY OF EXOGENOUS PROTEINS TO THE CYTOSOL AND USES THEREOF

REFERENCE TO CROSS-RELATED APPLICATIONS

This application is a Divisional Application of U.S. application Ser. No. 10/473,190 filed Feb. 17, 2004, now U.S. Pat. No. 7,754,219, which is a 35 U.S.C. §371 entry of PCT/US02/09680, filed Mar. 28, 2002, which claims benefit under 35 U.S.C. §119(a) of 60/279,366 filed on Mar. 28, 2001, the contents of which are incorporated herein in their entirety by reference.

GOVERNMENT SUPPORT

This invention was supported by National Institutes of Health grant AI47539 and the government of the United States has certain rights thereto.

FIELD OF THE INVENTION

The present application is directed to a method of delivering exogenous proteins to the cytosol, novel fusion proteins and uses thereof.

BACKGROUND OF THE INVENTION

Much attention has focused on methods for generating immune reactions. One class of immune reaction to foreign antigens is the production of antibodies, typically referred to as humoral immunity. A second form of immune reaction results from the presentation of antigen by an antigen presenting cell (APC). This type of immune reaction is broadly referred to as cell mediated immunity (CMI), or T cell responses. Although both types of immune responses are important, considerable attention has recently focused on CMI. In dealing with infectious diseases such as AIDS, caused by the Human Immunodeficiency Virus (HIV), the antibody responses to the virus and portions thereof have not proven sufficient to confer immunity. Similarly, in dealing with exogenous proteins associated with many malignancies, the antibody responses have also not proven sufficient. Thus, speculation has focused on generating CMI responses.

In order to elicit CMI, an antigen must be bound to a major histocompatibility complex (MHC) class I or II molecule on the surface of the APC. The class I molecules typically present antigens externally, such as endogenous proteins, those from viral infections, and tumor antigens. Antigen-specific T cells typically recognize infected target cells when the pathogen-derived (or cancerous) peptide epitopes (usually 8 to 10 amino acids) are presented by molecules encoded by the host class I MHC. These epitopes are derived from cytoplasmic proteins cleaved by the proteosome into small peptide fragments. These are then transported into the lumen of the endoplasmic reticulum (ER), where they complex with newly synthesized MHC-I molecules and are subsequently transported to the cell surface, where recognition by T cells occurs. Antigens in the extracellular fluid (exogenous antigens) generally do not gain access into this processing compartment in most cells. Thus, a significant challenge to eliciting CMI with a vaccine is the delivery of exogenous antigens to the cytosol for presentation by MHC class I molecules. It would be desirable to be able to generate vaccines to a wide variety of infectious diseases, such as HIV, as well as cancers, such as prostate cancer, breast cancer and melanoma.

For example, growing evidence suggests that CMI plays an essential role in controlling HIV infection (Ogg et al., *Science* 279:2103-6 (1998); Schmitz et al., *Science* 283:857-60 (1999); Brodie et al., *Nat. Med.* 5:34-41 (1999)). Individuals who have been exposed to HIV but remain uninfected often have antiviral CMI but no antibody response. The viremia of primary infection resolves as viral specific cytotoxic T lymphocytes (CTL) develop, before the development of specific antibodies (Letvin, *Science* 280:1875-96 (1998)). These data illustrate the central role CMI plays in controlling HIV infection.

Many tumors are associated with the expression of a particular protein and/or the over-expression of certain proteins. For example, prostate cancer is associated with elevated levels of protein such as Prostate Specific Antigen (PSA). Breast cancers can be associated with the expression and/or over-expression of protein such as Her-2, Muc-1, CEA, etc. Thus, considerable attention has been aimed at trying to generate immune responses, particularly developing CMI, to such antigens in the treatment of such malignancies.

Approaches to developing cell mediated immunity to infectious diseases have included using the entire infectious agent, for example, by making genetically engineered inactivated viruses or using a killed infectious agent. Another approach has been subunit vaccines, which is presenting one or more antigens (but not the entire virus) to a subject.

In order to generate CMI, antigen must be delivered to the interior of the cell. Exogenous proteins are poorly taken up by the cell. Accordingly, the preferred method has been using procedures such as viral vectors, liposomes, naked DNA or a similar approach. However, such approaches have many drawbacks. For example, many recombinant viruses generate antigenic reactions themselves, upon repeated administration. Since standard forms of generating immune reactions typically require an initial injection, referred to as the prime, and subsequent injections, referred to as boosts, to achieve a satisfactory immunity, this can be a serious problem. Moreover, while much attention has been placed on improving the safety of viral vectors, there are always certain risks. For example, many of the target populations, such as those infected with HIV, may have a weakened immune system. Thus, certain viral vectors that are perfectly safe in many individuals may pose some degree of risk to these individuals. Methods of delivering protein to cells have also not proven entirely satisfactory as of this time. Accordingly, there is a need for new and simple methods to deliver an antigen to the cytosol to stimulate CMI.

In trying to develop CMI responses, there have also been technical problems with the difficulty in measuring these responses.

Current available laboratory assays to detect cell-mediated immune responses have serious shortcomings, especially when applied to large vaccine efficacy trials in various clinical settings. This is because the available equipment and technical support required to measure CMI using current techniques are often minimal in the setting where they are required, in the field. CTL are thought to play a crucial role in controlling HIV-1 infection, and many HIV-1 vaccine candidates are designed to stimulate T cell responses as well as neutralizing antibodies. However, the standard laboratory methods for detecting CMI, such as HIV-specific CTL, are complex, time consuming, and often restricted to highly specialized facilities. An improved method for measuring T cell responses will have a significant effect on the development of all T cell dependent vaccines or immune therapies. This strategy can potentially be applicable to other fields of research where CMI responses are known to play an important role in prevention and control of the diseases.

One difficulty in reliably detecting CMI response in vitro results from the unique requirement for antigen presentation. As described above, the delivery of exogenous proteins to the cytosol for presentation to T cells by MHC class I molecules represents a significant challenge. This physical partition of the class I pathway has been a major barrier to detect T cell responses in vitro. Consequently, most of the current laboratory methods in measuring CMI utilize live viral or bacterial vectors to deliver antigens into cytosol, among which recombinant pox such as vaccinia viruses are the most commonly used. Another approach is to externally load MHC-I molecules on surface of target cells with synthetic peptides (10 to 20 amino acids) derived from known CTL epitopes. These methods have serious limitations in general clinical uses. The use of a live viral vector, such as a recombinant vaccinia virus, requires trained and immunized laboratory personnel, including minimum containment facilities as precautionary safety measures. Synthetic peptides are not only prohibitively expensive, but the design of the "universal" peptide profile that fit the diversified MHC-I molecules in various populations is extremely difficult. The challenge for the development of assays to measure T cell responses is, therefore, to deliver large pieces of exogenous antigens into cytosol without resorting to live recombinant viral or bacterial vectors.

Accordingly, it would be desirable to have kits that could be used for measuring CMI in vitro. It would be particularly desirable to have kits that could be readily used in remote locations such as Africa, India and Asia, where there are many proposals to test a number of vaccine candidates such as vaccines against HIV.

We have now discovered that a family of bipartite protein exotoxins, such as *Bacillus anthracis*, contains fragments that can be used for the delivery of exogenous antigens, such as proteins, to the cytosol. One preferred protein fragment from these proteins is from the N-terminal portion that contains the protective antigen (PA) binding domain, but not those portions resulting in toxicity to the cell. More preferably, that fragment has been modified to remove the specific domain that binds to PA.

*B. anthracis* is the causative agent of anthrax in animals and humans. The toxin produced by *B. anthracis* consists of two bipartite protein exotoxins, lethal toxin (LT) and edema toxin. LT is composed of protective antigen (PA) and lethal factor (LF), whereas edema toxin consists of PA and edema factor (EF). None of these three components, PA, LF, and EF, alone is toxic. Once combined however, edema toxin causes edema and LT causes death by systemic shock in animals and humans. Consistent with its critical role in forming both toxins, PA has been identified as the protective component in vaccines against anthrax. The molecular mechanism of anthrax toxin action is currently hypothesized as follows: PA is a 735-amino acid polypeptide that binds to the surface of mammalian cells by cellular receptors. Once bound, PA is activated by proteolytic cleavage by cellular proteases to a 63-kDa molecule capable of forming a ring-shaped heptamer in the plasma membrane of the targeted cell (FIG. 1). The PA heptamer then binds either EF or LF, which are internalized by endocytosis. After endosomal acidification, PA enables EF or LF to enter the cytosol, presumably by means of a pore formed by the heptamer. Within the cytosol, EF acts as an adenylate cyclase to convert ATP to cAMP. Abnormally elevated levels of cAMP perturb cellular metabolism.

The action of LF in the cytosol causes the death of host cells by a mechanism that is not well understood. LF induces over-production of a number of lymphokines, contributing to lethal systemic shock in host animals. Recent studies also show that LF has two enzymatic activities: it can act as a zinc metalloprotease, and it inactivates the mitogen-activated protein kinase. Although it is still not clear how these two enzymatic activities of LF are connected, both are required for LF toxicity. It has previously been reported that anthrax toxin B moieties may be used to deliver eptiopes which in turn elicit an antibody response by the immune system, in the presence of PA (WO 97/23236).

LF is a 776-aa polypeptide, and the functional domain for both enzymatic activities is located between amino acids 383 and 776 (FIG. 2A; SEQ ID NO: 1). The N-terminal truncated LF (LFn) polypeptide is a 255 amino acid polypeptide (corresponding to residues 34-288 of SEQ ID NO: 2). The 255 amino acid LFn polypeptide part is derived from a precursor protein of 1-288 residues as shown in FIG. 2B (SEQ ID NO: 2), where the first 1-33 amino acids correspond to the signal peptide. Without the catalytic domain, LFn polypeptide (residues 34-288 of SEQ ID NO: 2) completely lacks any toxic effect when mixed with PA and added to cultured macrophages or when injected into animals. It does, however, still bind to PA effectively. The PA binding domain of the LFn polypeptide (i.e. where the LFn polypeptide is residues 34-288 of SEQ ID NO: 2, and thus the first 1-149 N-terminal amino acids of the LFn polypeptide are residues 34-184 of SEQ ID NO: 2.

SUMMARY OF THE INVENTION

The present invention provides methods of delivering exogenous antigens to the cytosol, novel fusion proteins, and uses thereof.

We have now further found that one can use a transport factor that is lethal factor modified to inactivate toxin domains, fragments thereof such as LFn and fragments of LFn, such as a fragment containing the carboxy portion of that fragment, as a transport factor, fused to a target antigen, without PA to deliver the antigen to the cytosol. Preferably, the transport factor is LFn or a fragment thereof. One preferred group is LFn fragments do not contain the PA binding domain. More preferably, the transport factor is an LFn fragment. For example, the 60 carboxy most amino acids of LFn can be used as a transport factor; still more preferably the 80 carboxy-most amino acids. One can also use other fragments. For example, one can use fragments containing more of the lethal factor protein as long as one inactivates the toxin portion. Preferably the transport factor fragment contains a portion of the 80 carboxy-most amino acid residues of LFn and contains other portions of the fragment as long as those portions containing toxicity are removed. Preferably the fragment is 350 amino acids or less, still more preferably it is 300 amino acids or less, even more preferably it is 250 amino acids or less. One preferred fragment is 105 amino acids or less. A more preferred fragment is 80 amino acids or less. This transport factor is then linked to the antigen you wish to bring to the cytosol. This can be done by techniques well known in the art. For example, one could prepare fusion proteins containing the antigen or antigens that one wants to bring to the cytosol of the cell.

The preferred methods of the invention are characterized by novel polypeptides which elicit in treated animals the formation of a cell mediated immune response.

This invention provides DNA sequences that code for the novel fusion polypeptides of the invention, recombinant DNA molecules that are characterized by those DNA sequences, unicellular hosts transformed with those DNA sequences and molecules, and methods of using those sequences, molecules and hosts to produce the novel polypeptides and CMI immune response to desired antigens this invention.

In another preferred embodiment, this invention provides a pharmaceutical composition comprising one or more novel fusion peptides of this invention. Such a composition is effective in eliciting cell mediated immune responses. In one preferred embodiment it can be used as a vaccine. In another embodiment, these fusion proteins can be used to create producer cells, preferably bacterial producer cells for a variety of proteins, particularly proteins that have proven difficult to express in such cells.

In another preferred embodiment, this invention provides a method for measuring cell mediated immune responses.

In a further preferred embodiment, this invention provides a kit for measuring cell mediated immune responses in vitro.

BRIEF DESCRIPTION OF THE DRAWINGS

FIGS. 2A-C show the amino acid sequence of various lethal fragment (LF) polypeptides. FIG. 2A shows the full length amino acid sequence of LF, with the first 1-33 residues constituting the signal peptide, and the LF polypeptide beginning at residue 34 (SEQ ID NO: 1). FIG. 2B shows the precursor LFn protein of 1-288 residues, with residues 1-33 constituting the signal peptide, and residues 34-288 constituting the LFn polypeptide. (LFn corresponds to residues 34-288 of SEQ ID NO: 2 and the precursor LFn protein corresponds to residues 1-288 of SEQ ID NO: 2). FIG. 2C shows the sequence of amino acids 185-288 of lethal factor, which corresponds to SEQ ID NO: 3 herein and is sometimes referred to as Fragment 3.

FIG. 3A shows activity of a Nef-specific clone (KM) was tested against B60 restricted target cells incubated overnight with Nef recombinant vaccinia vectors, PA and LFnNef or LFn Nef alone. Background/control for each target was included (control, PA-LFn, LFn). FIG. 3B shows Env-specific CTL clone (SP 511) recognizes targets labeled with LFnEnv in a dose dependent fashion and was again PA-independent. Control used were peptide Env 106B(100 mg/ml). Dose of LFn construct is listed as mg/ml (LfnEnv 5=5 m/ml of LfnEnv).

FIGS. 7A-B are FACS plots that show LFn-HIV expression in intracellular flow-based assay. Intracellular production of IFN-g in Nef-specific clone (KM)(A) as well as from PBMC of a seropositive individual (AC2) with Env-specific CTL activity (B). Unstimulated cells were used as negative control (1) and recombinant vaccinia viruses as positive control (2) LfnNef and LfnEnv were used respectively (3).

FIG. 11A-C show fields of cells examined by confocal microscopy for GFP.

FIGS. 12 A-D show fields of cells examined by confocal microscopy for LAMP-2 immunostaining; FIGS. 12 E-H show the corresponding fields examined by confocal microscopy for LN-GFP immunostaining. A third image is presented for each field by super-imposing the LF-GFP immunostaining image with the LAMP-2 immunostaining image of the same cells (FIGS. 12I-L).

FIGS. 13 A-D show fields of cells examined by confocal microscopy for EEA-1 immunostaining; FIGS. 13 E-H show the corresponding fields examined by confocal microscopy for LN-GFP immunostaining. A third image is presented for each field by super-imposing the LN-GFP-immunostaining image with the EEA-1 immunostaining image of the same cells (FIGS. 13 I-L).

FIGS. 14 A-B show fields of cells examined by confocal microscopy for red color (anti-Golgi antibody); FIGS. 14 C-D show the corresponding fields examined by confocal microscopy for green color (LN-GFP). A third image is presented for each field by super-exposing the green image with the red image of the same cells (FIGS. 14 E-F).

FIG. 15 shows co-localization of GFP and anti-20s immunofluorescence to indicate the proteosome. Conditions were similar to those used in FIG. 10 except HeLa cells were uncubated with 40 μg/ml LNgfp for 2 hours. FIG. 15 A-D show fields of cells examined by confocal microscopy for anti-20s antibody immunostaining; FIG. 15 E-H show the corresponding fields examined by confocal microscopy for LN-GFP immunostaining), respectively. A third image is presented for each field by super-imposing the LN-GFP immunostaining image with the anti-20s immunostaining image of the same cells (FIG. 15I-L). By comparing the different images in FIGS. 12-15, the super-imposed images that have the most GFP-localization with the other marker are those shown in FIG. 15 in which the intracellular LFn-GFP overlap significantly with the cellular proteosome.

FIGS. 16 A-F show incubation of HeLa cells with LN-GFP in the absence of PA; FIGS. 16 G-L show incubation of HeLa cells in the presence of PA. FIGS. 16 A-B and G-H show fields of cells examined by confocal microscopy for anti-20s antibody immunostaining; FIGS. 16 C-D and I-J show the corresponding fields examined by confocal microbscopy for LN-GFP immunostaining, respectively. A third image is presented for each field by super-imposing the LF-GFP image with the anti-20s immunostaining of the same cells (FIGS. 16 E-F and K-L).

DETAILED DESCRIPTION OF THE INVENTION

Figure 1:
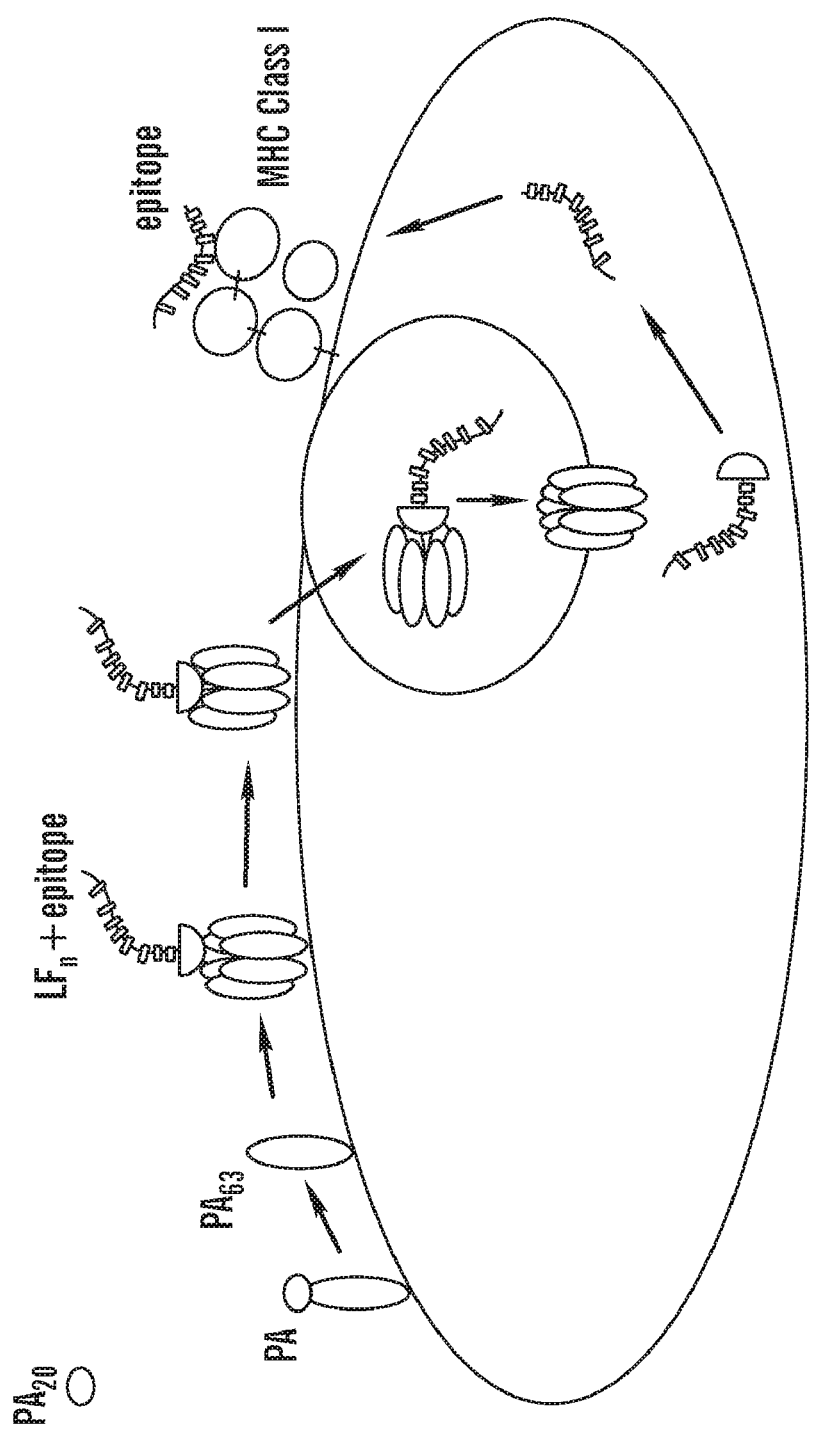
FIG. 1 is a drawing depicting the PA-mediated entry of LFn into a cell via endocytosis, and subsequent presentation by MHC Class I molecules.

We have now discovered a method for delivering exogenous proteins to the cytosol, by binding a target antigen (such as a protein) to a transport factor that contains a fragment of a bipartite protein exotoxin in the absence of a protective antigen (PA). Preferably, the target antigen is fused to the transport factor. Preferably, the transport factor is the protective antigen binding domain of lethal factor from B. anthracis, consisting of amino acids 1-288 of SEQ ID NO:2 or a fragment thereof that does not contain the PA binding domain such as the carboxy portion of amino acids 1-288 of SEQ ID NO: 2. For example, a fragment of about the 80 carboxy-most amino acids of preferred group of amino acid LFn 1 amino acid fragments for the transport factor comprises at least 80 amino acids that show at least 80% homology to SEQ ID NO: 2 using Blast on default settings. Still more preferably, the fragment has at least 90% homology thereto, even more preferably, it has at least 95% homology thereto. Preferably, that fragment does not contain the PA binding domain. A preferred transport factor is the LFn fragment or a portion thereof. More preferably, the transport factor comprises at least the 60 carboxy-most amino acids of LFn but not the PA binding domain. One preferred fragment has about 105 amino acids or less from the carboxy portion of SEQ ID NO:2.

The target antigen can include any molecule for which it would be desirable to elicit a CMI response, including viral antigens and tumor antigens.

One embodiment of the invention provides a composition including the novel fusion polypeptide for generating. Another embodiment of the invention includes assays for measuring CMI responses by delivering exogenous proteins to the cytosol. A preferred embodiment provides kits for measuring CMI responses.

Novel fusion polypeptides of the present invention comprise a transport factor linked to a target antigen. The transport factor can include a fragment of any bipartite protein exotoxin that delivers the protein to the cytosol in the absence of protective antigen without including any fragments that are toxic. This transport method is independent of the PA associated pathway and thus PA is unnecessary. A preferred exotoxin is Lethal Factor (LF) of B. anthracis (SEQ ID NO:1) (FIG. 2A). The PA binding domain of LF, is part of LFn, or a fragment thereof where the LFn or fragment thereof can be used to transverse a cell membrane, wherein LFn consists of amino acids 1-255 of LF (i.e. residues 34-288 of SEQ ID NO: 1), and wherein LFn polypeptide corresponds to residues 34-288 SEQ ID NO: 2 (FIG. 2B). Any fragment of LFn polypeptide can be used as the transport factor. Preferably it does not contain the PA binding domain, which is present in the N-terminal half of LFn polypeptide (aa 1-149 of the LFn polypeptide, e.g., residues 34-183 of SEQ ID NO: 2). One preferred fragment has 105 amino acids or less from the carboxy portion of SEQ ID NO:2. Preferably, the 60 carboxy-most amino acids, still more preferably the 80 carboxy-most amino acids. A preferred transport factor is Fragment 3 (SEQ ID NO:3) (FIG. 2C).

One can also use other fragments as the transport factor. Preferably, the transport factor is 350 amino acids or less, still more preferably, 300 amino acids or less, even more preferably, it is 250 amino acids or less.

Other fragments preferred as the transport factor have at least 55% homology to Fragment 3 of LFn (SEQ ID NO:3) (FIG. 2C). For example, a fragment of Edema Factor of *B. anthracis* has approximately 57% homology to Fragment $3_g$ using Blast on default settings. More preferably, it has at least 65% homology thereof; still more preferably, it has at least 75% homology thereto; even more preferably, it has at least 80% homology thereto; even more preferably, it has at least 90% homology thereto; even more preferably, it has at least 95% homology thereto.

The transport factor is linked to any antigen whose delivery to the cytosol is desired. Preferably, the linkage is a chemical linkage, for example a peptide bond to form of a fusion protein. However, other linkers known in the art can be created. For example, a linker unit can be part of the transporter that can then be chemically linked to the target antigen. Preferred antigens include viral, bacterial, parasitic, and tumor associated antigens. Preferred viral antigens include proteins from any virus where a cell-mediated immune response is desired. Particularly preferred viruses include HIV-1, HIV-2, hepatitis viruses (including hepatitis B and C), Ebola virus, West Nile virus, and herpes virus such as HSV-2. Preferred bacterial antigens include those from *S. typhi* and *Mycobacteria* (including *M. tuberculosis*). Preferred parasitic antigens include those from *Plasmodium* (including *P. falciparum*).

Preferred tumor antigens include those epitopes which are recognized in eliciting T cell responses, including but not limited to the following: prostate cancer antigens (such as PSA, PSMA, etc.), breast cancer antigens (such as HER2/neu, mini-MUC, MUC-1, HER2 receptor, mammoglobulin, labyrinthine, SCP-1, NY-ESO-1, SSX-2, N-terminal blocked soluble cytokeratin, 43 kD human cancer antigens, PRAT, TUAN, Lb antigen, carcinoembryonic antigen, polyadenylate polymerase, p53, mdm-2, p21, CA15-3, oncoprotein 18/stathmin, and human glandular kallikrein), melanoma antigens, and the like.

Preferably, when one is trying to generate an immune response in a subject, an immune adjuvant is also used. Adjuvants are known in the art and include cytokines such as IL-2, Ig-IL-2, CM-CSF, CpG, RIBL Detox (Ribi Immunochemical), QS21 (Cambridge Biotech), incomplete Freund's adjuvant and others. We have unexpectedly found that although Alum can actually inhibit CTL induction, in the present system, Alum is preferred for stimulating specific CTL.

The methods of the present invention can also be used to identify additional cancer antigens, by making libraries of tumor antigens fused to the transport factor in conjunction with the CMI assays, described below.

The target antigen can be of any size that allows delivery to the cytosol. Preferably, the target antigen is less than 750 amino acids, still more preferably, less than 600 amino acids, even more preferably, less than 500 amino acids.

Figure 8A:
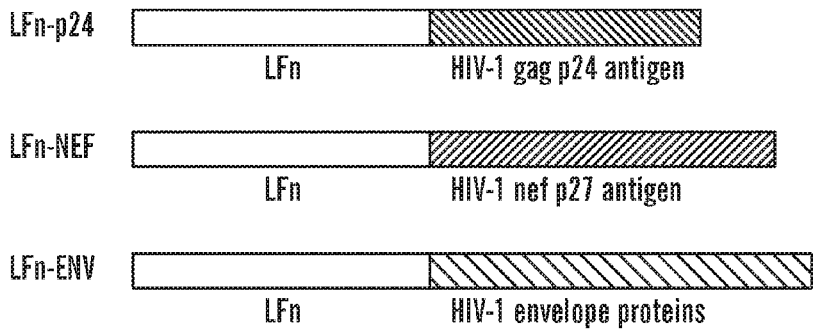
FIGS. 8A and B are drawings depicting LFn fusion proteins.
Figure 8B:
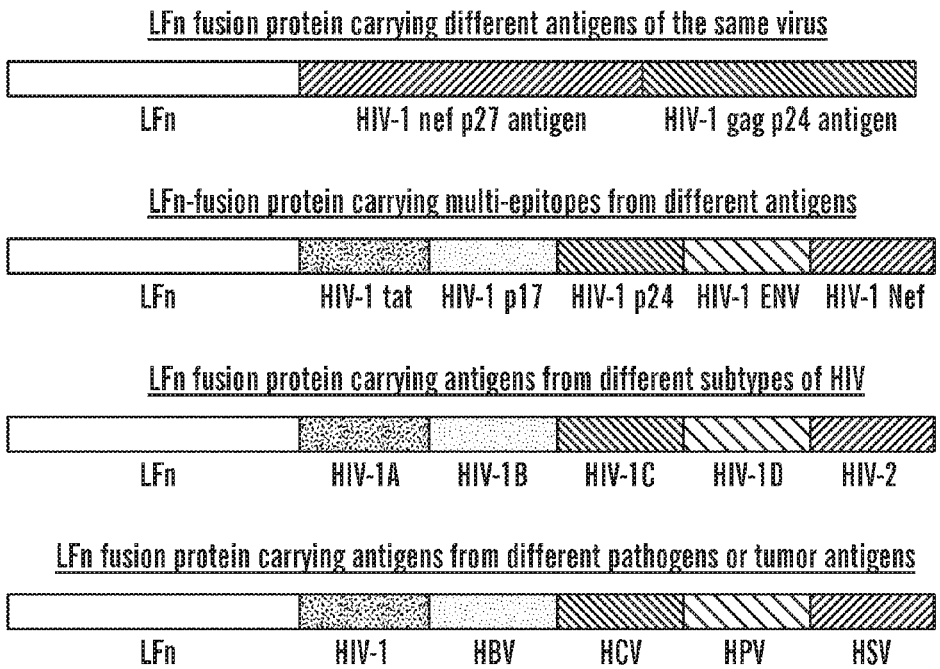
Figure 9:
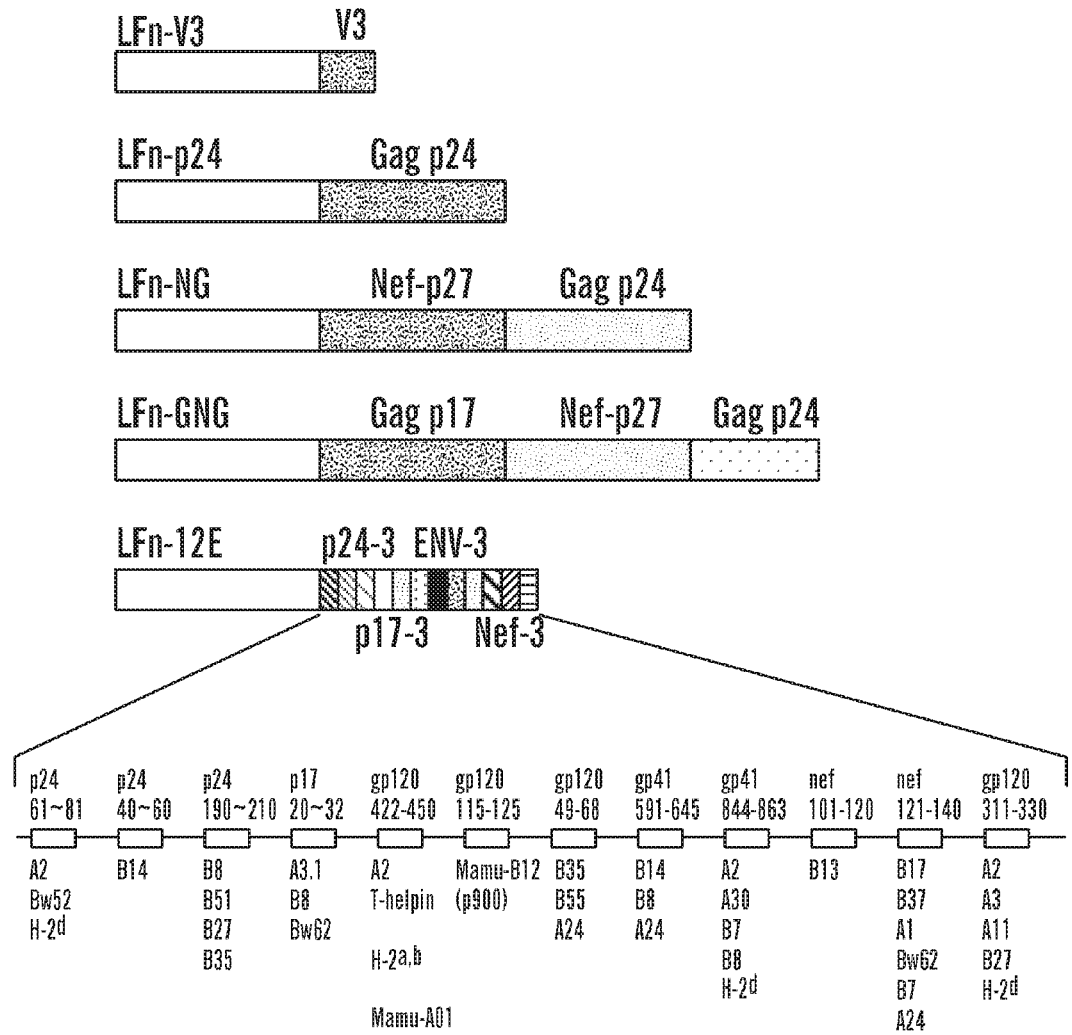
FIG. 9 is a series of drawings depicting LFn fusion proteins.
Figure 10A:
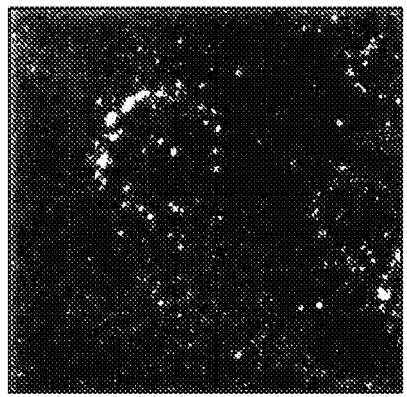
As shown in FIGS. 10A-D, GFP immunostaining was visible in cells treated with LFn-GFP for one hour, suggesting the LFn-GFP can indeed enter into cells.
Figure 10B:
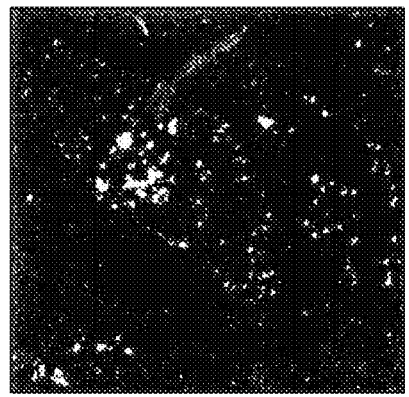
Figure 10C:
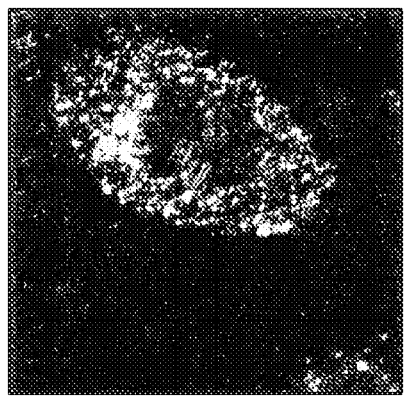
Figure 10D:
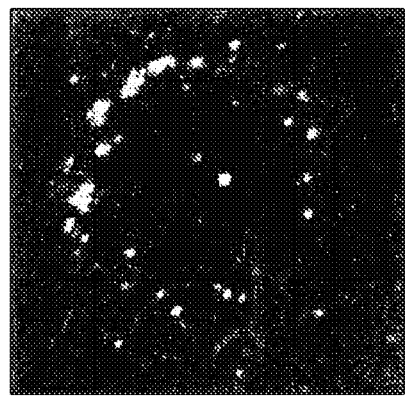
Figure 10E:
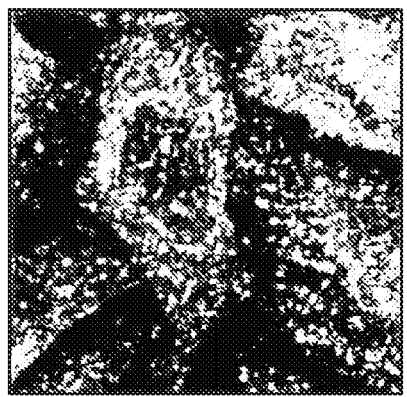
FIG. 10 shows cellular uptake of LFn-GFP into CHO cells. CHO cells were cultured in collagen treated chamber slides to reach 80% confluence and were then incubated with purified LFn-GFP for one hour, followed by washing extensively with PBS and PBS plus proteases to remove membrane bound proteins. The cells were then stained with the anti-transferrin antibodies and fixed with paraformaldehyde. The slides were examined by confocal microscopy, with FIGS. 10A-10D showing GFP immunostaining and FIGS. 10E-10H showing anti-transferrin immunostaining. A third image is presented for each field by super-imposing the GFP immunostaining with the anti-transferring immunostaining of the same cells (FIG. 10I-10L). Consequently, co-localization of GFP in the same spot with the transferrin protein provides a reference that the location of GFP is inside the cells.
Figure 10F:
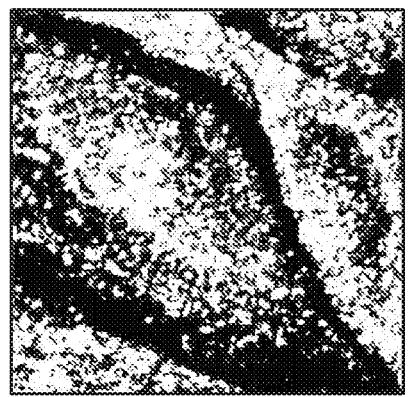
Figure 10G:
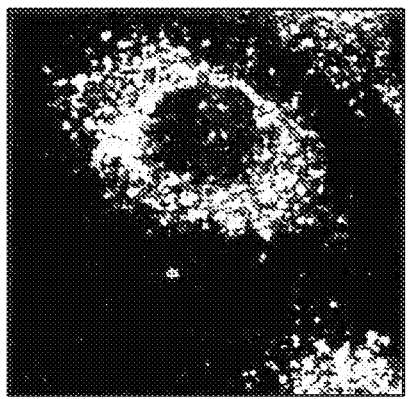
Figure 10H:
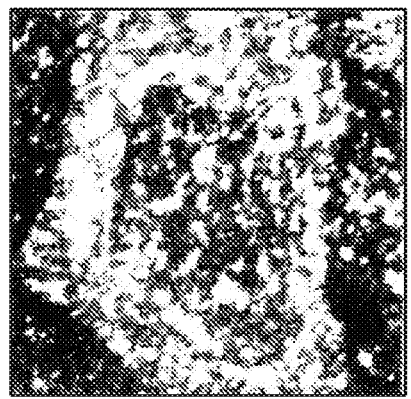
Figure 10I:
Figure 10J:
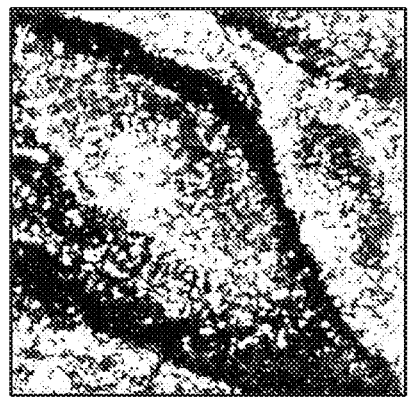
Figure 10K:
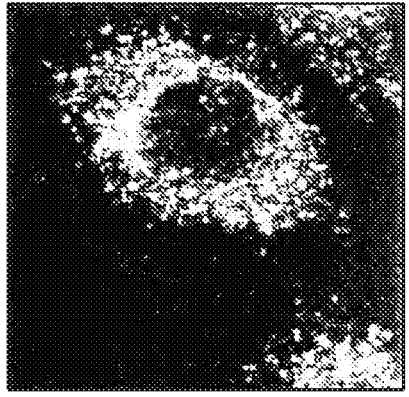
Figure 10L:
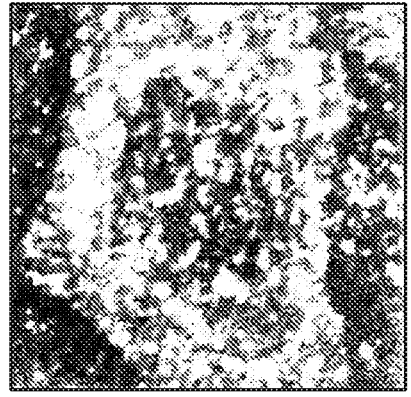
Figure 11A:
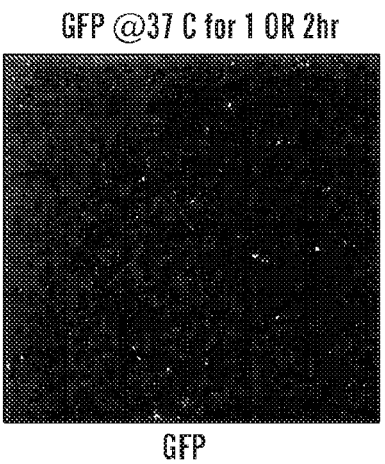
FIGS. 11A, D, and G show the results of incubating CHO cells with GFP for 1 hour.
Figure 11B:
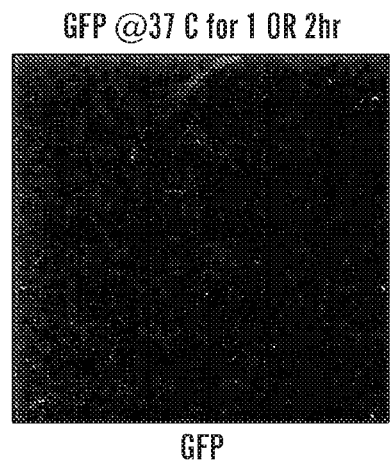
FIG. 11B-C, E-F, and H-I show the results of incubating CHO cells with GFP for two hours.
Figure 11C:
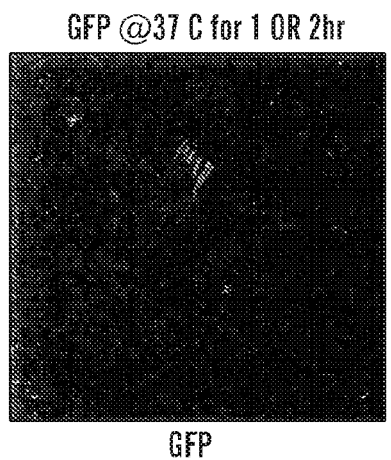
Figure 11D:
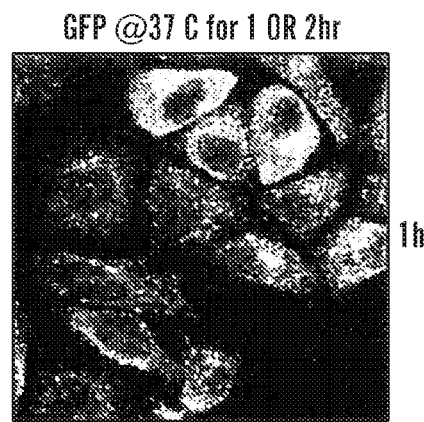
FIG. 11D-F show the corresponding fields examined by confocal microscopy for anti-transferrin, respectively. A third image is presented for each field by super-imposing exposing the GFP-immunostaining with the anti-transferring immunostaining of the same cells (FIG. 11G-I). GFP-treated cells showed few green spots (FIG. 11).
Figure 11E:
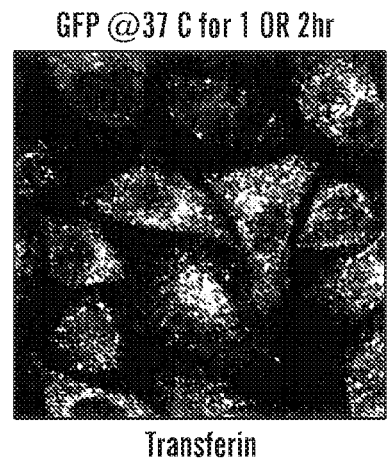
Figure 11F:
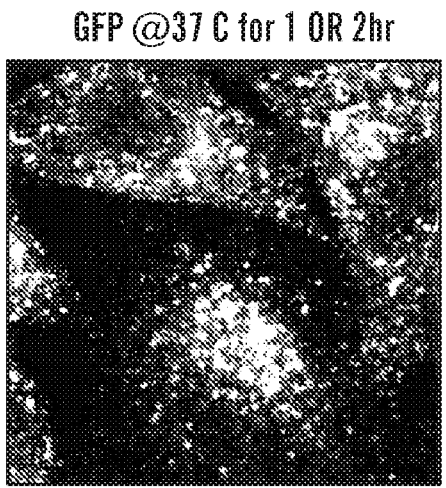
Figure 11G:
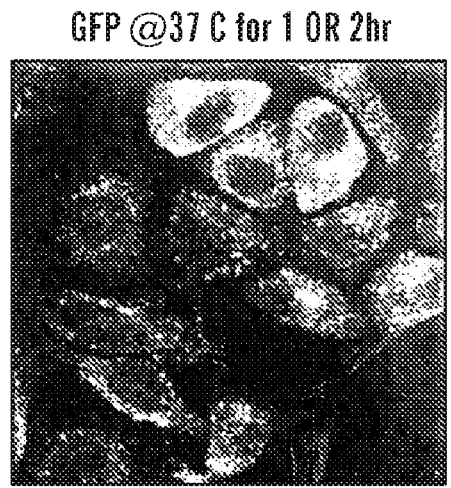
FIG. 11 shows cellular uptake of GFP into CHO cells, using conditions as described for FIG. 10.
Figure 11H:
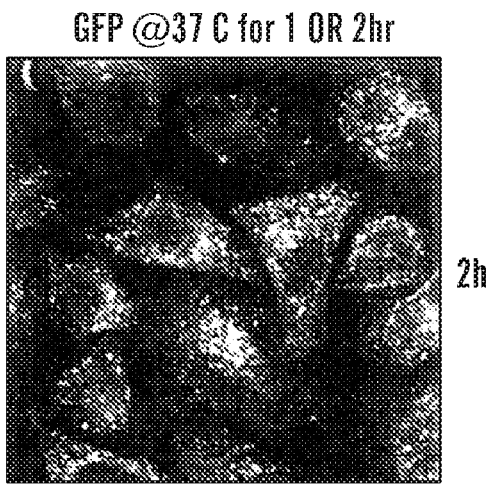
Figure 11I:
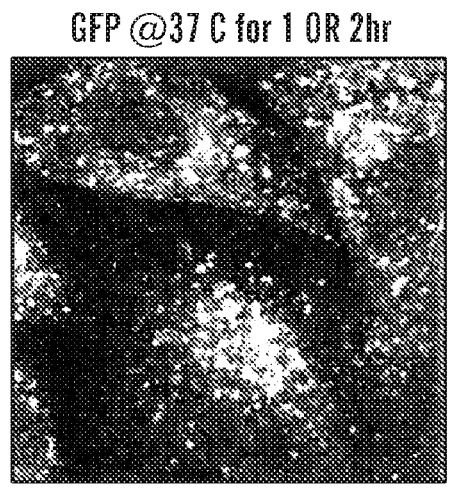
Figure 12A:
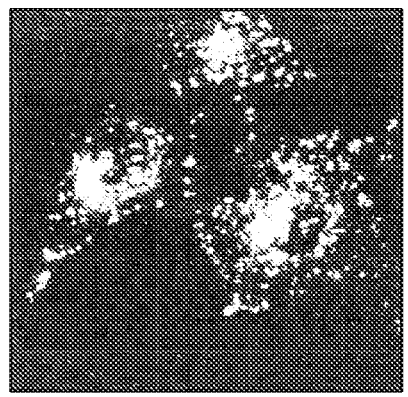
FIG. 12 shows co-localization of GFP and LAMP-2 immunofluorescence to indicate the lysosome, using the identical experimental procedures described above for FIG. 10.
Figure 12B:
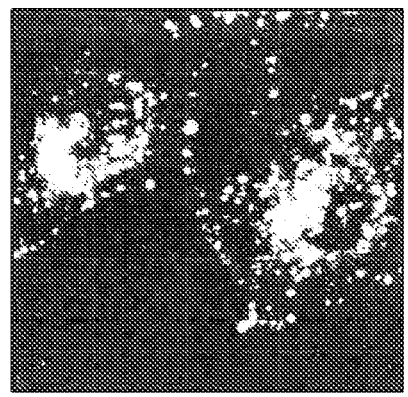
Figure 12C:
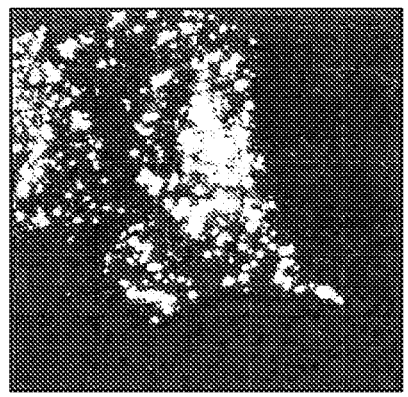
Figure 12D:
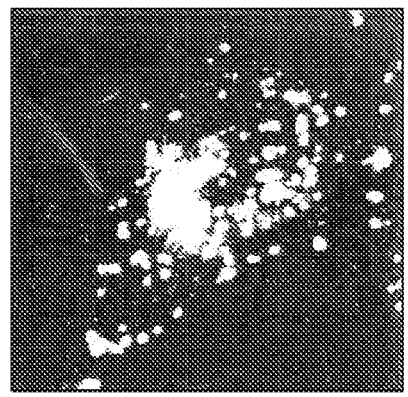
Figure 12E:
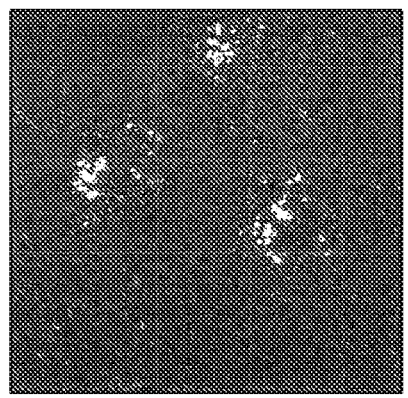
Figure 12F:
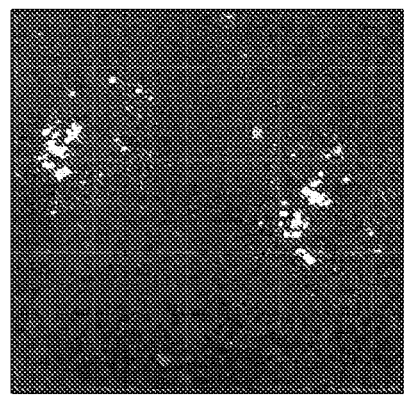
Figure 12G:
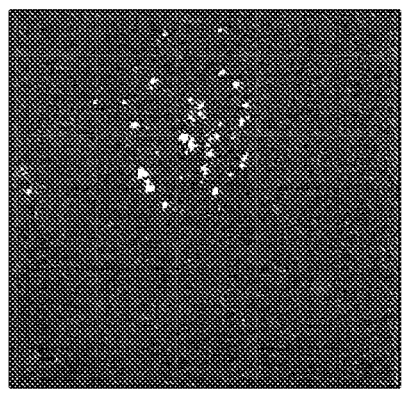
Figure 12H:
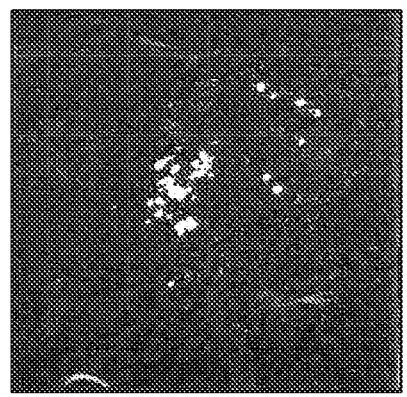
Figure 12I:
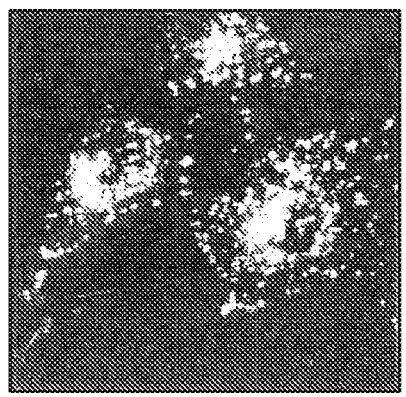
Figure 12J:
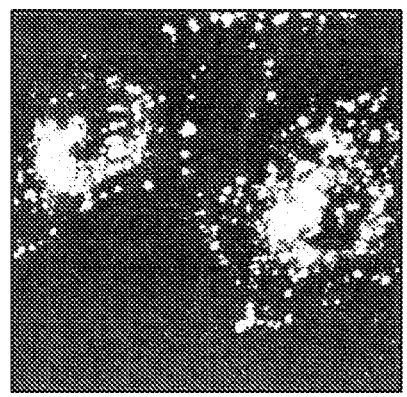
Figure 12K:
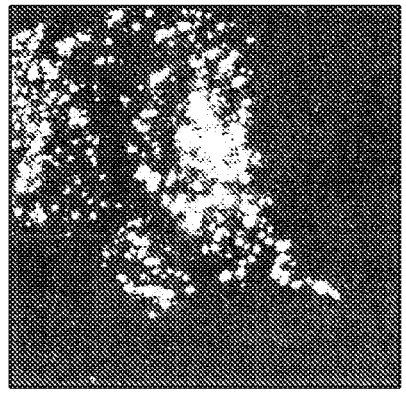
Figure 12L:
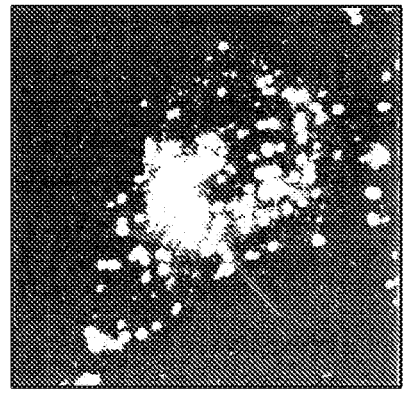
Figure 13A:
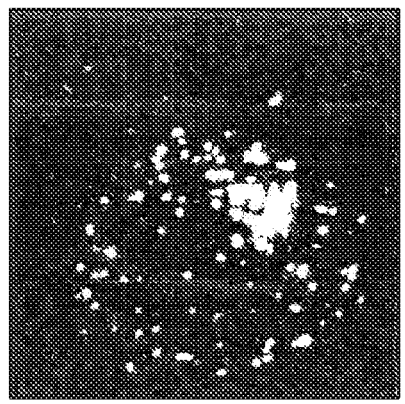
FIG. 13 shows co-localization of GFP and immunofluorescence to EEA-1 to indicate the endosome, using the identical experimental procedures described above for FIG. 10.
Figure 13B:
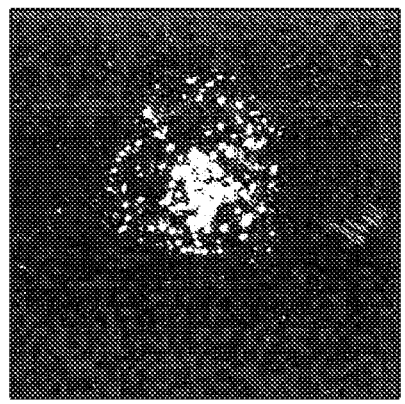
Figure 13C:
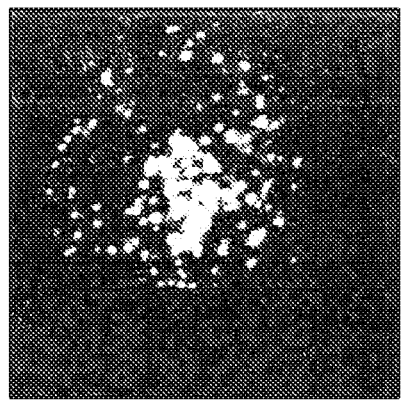
Figure 13D:
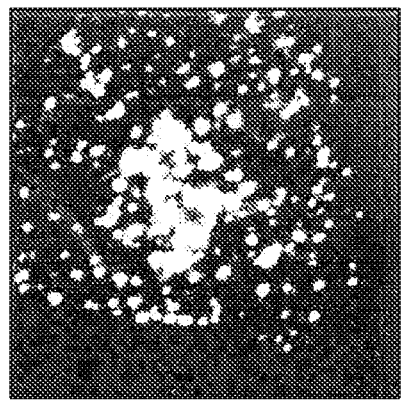
Figure 13E:
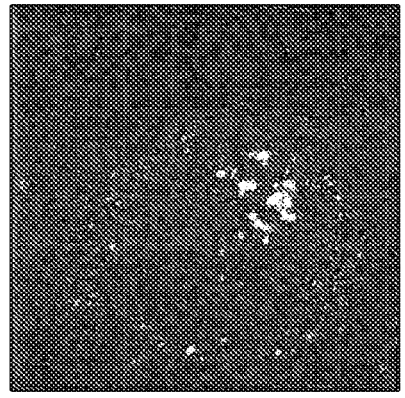
Figure 13F:
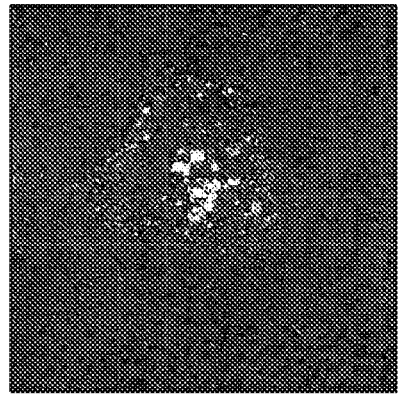
Figure 13G:
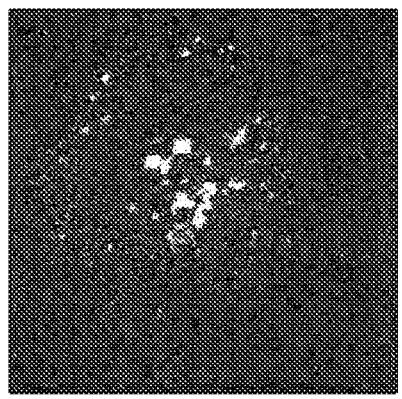
Figure 13H:
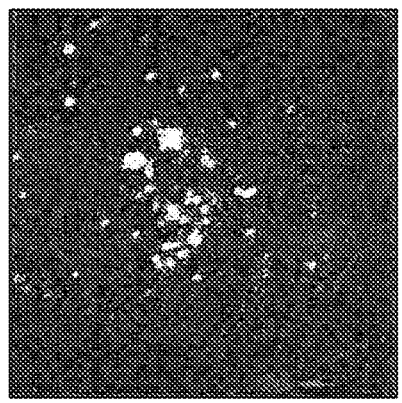
Figure 13I:
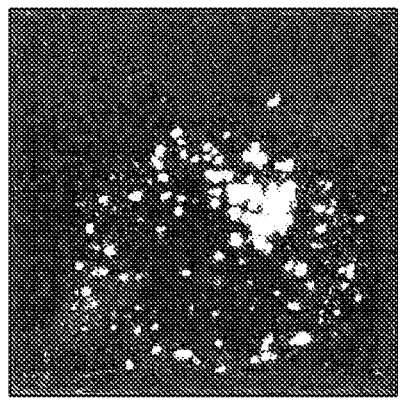
Figure 13J:
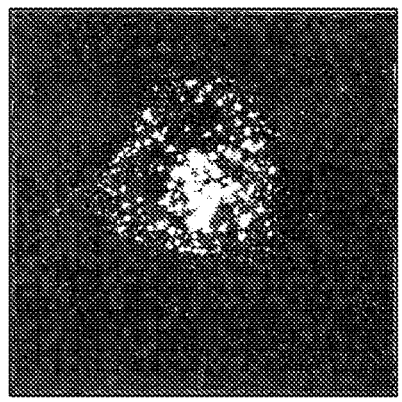
Figure 13K:
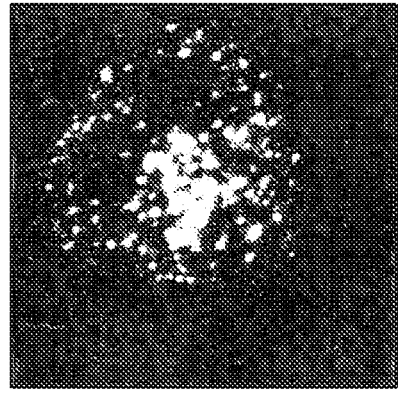
Figure 13L:
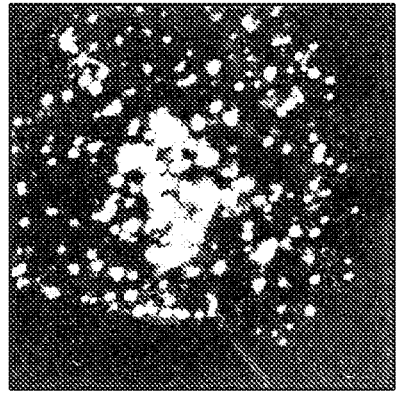
Figure 14A:
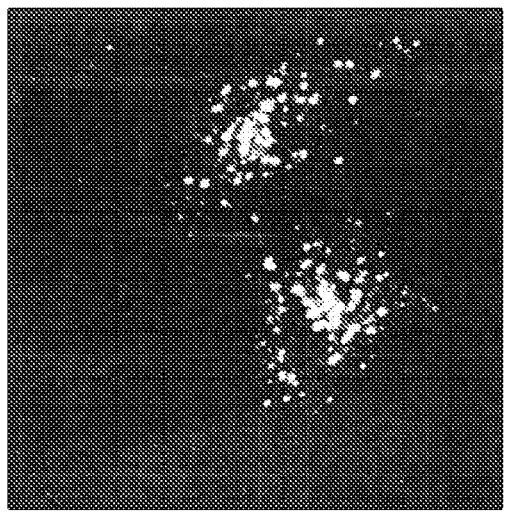
FIG. 14 shows co-localization of GFP and an anti-Golgi antibody, using the identical experimental procedures described above for FIG. 10.
Figure 14B:
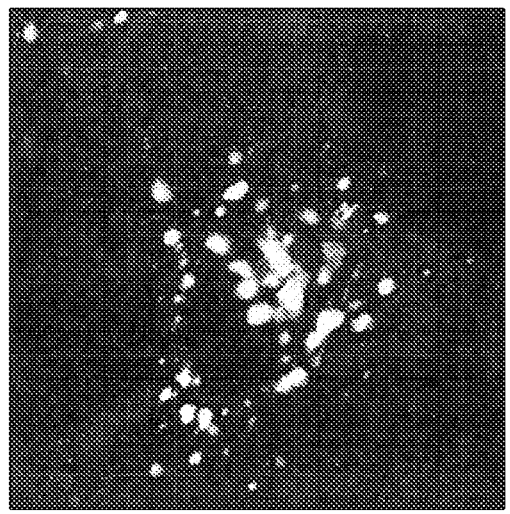
Figure 14C:
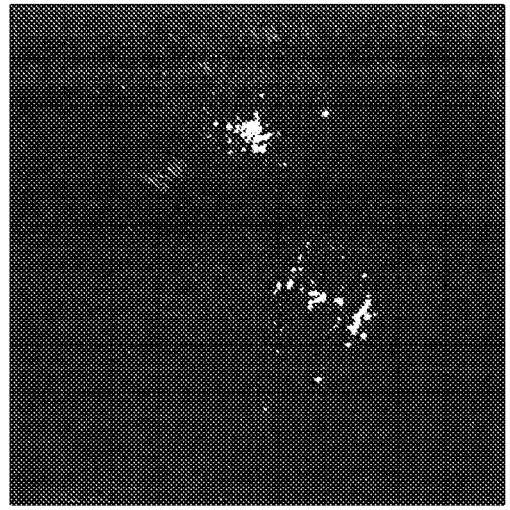
Figure 14D:
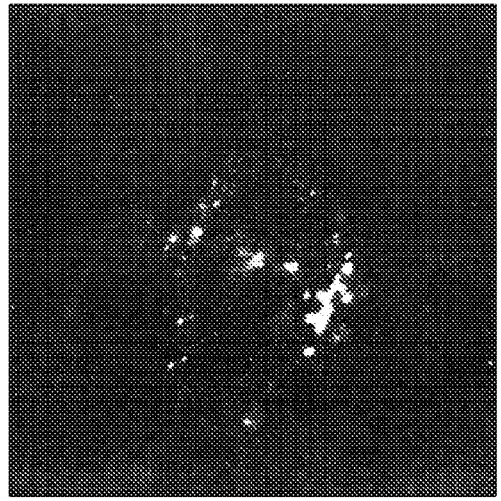
Figure 14E:
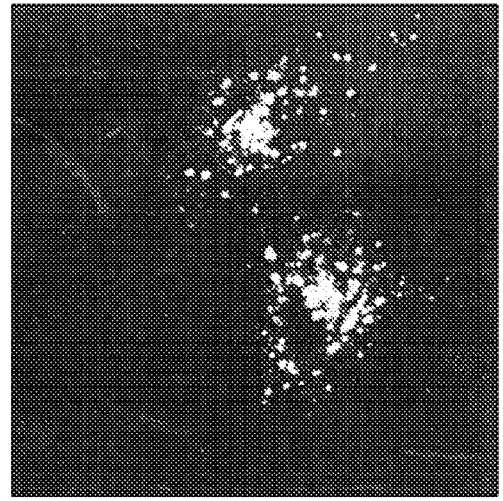
Figure 14F:
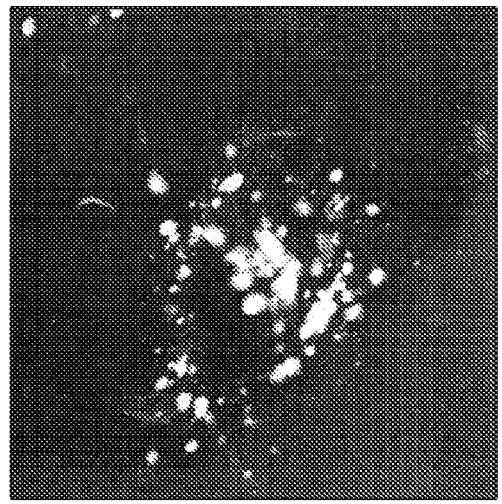
Figure 16A:
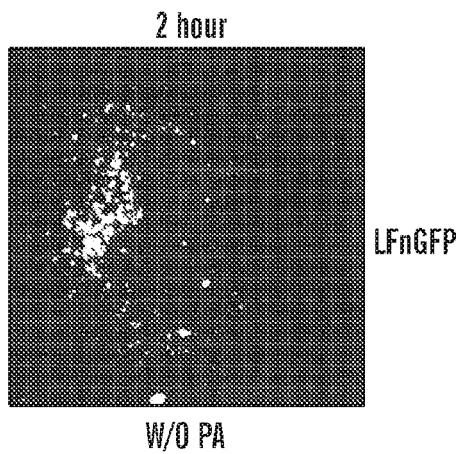
FIG. 16 shows that adding PA did not increase the number of green spots inside cells in comparison with those in the absence of PA, under conditions similar to those used in FIG. 15.
Figure 16B:
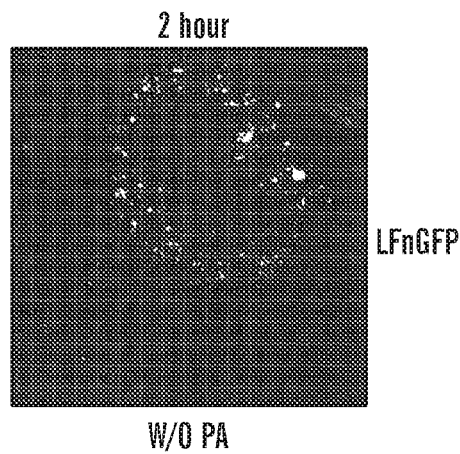
Figure 16C:
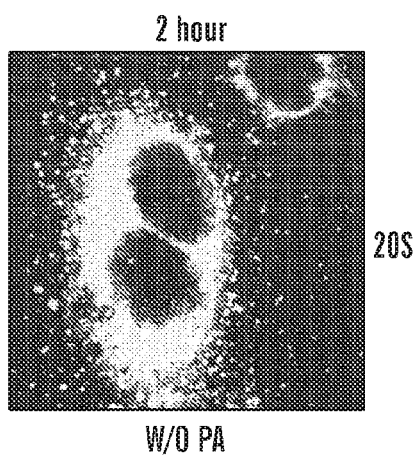
Figure 16D:
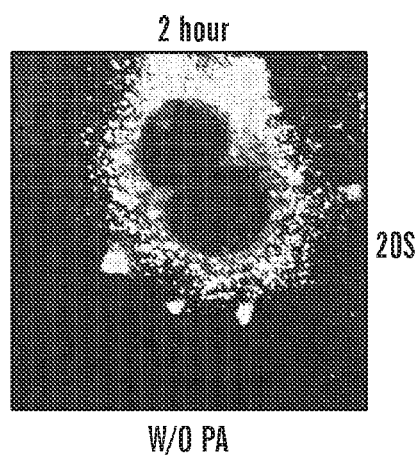
Figure 16E:
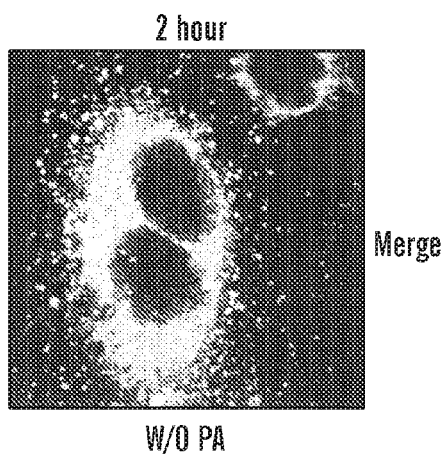
Figure 16F:
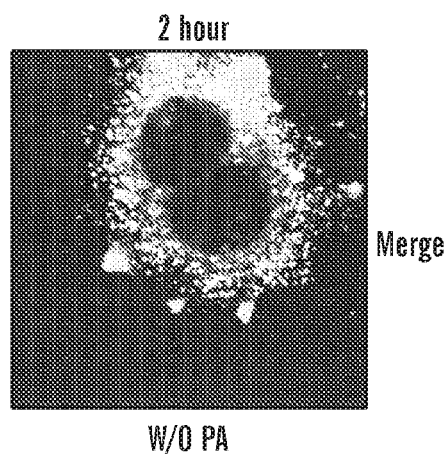
Figure 16G:
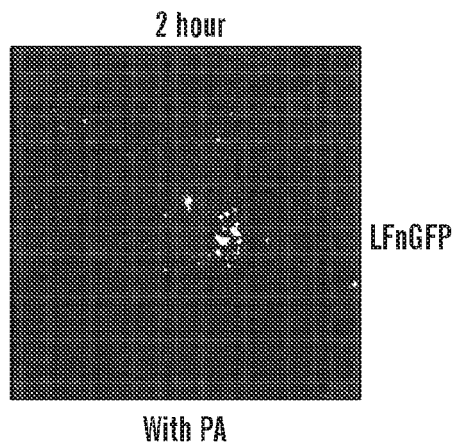
Figure 16H:
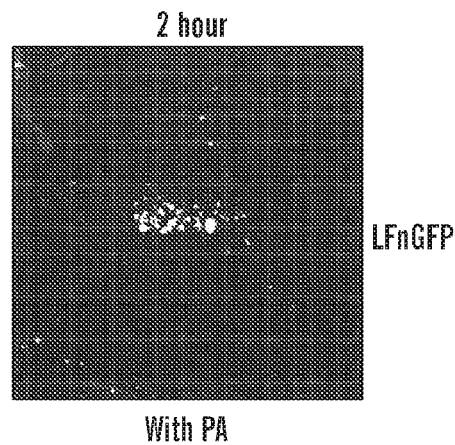
Figure 16I:
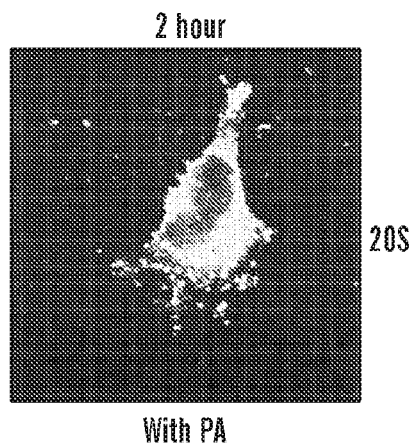
Figure 16J:
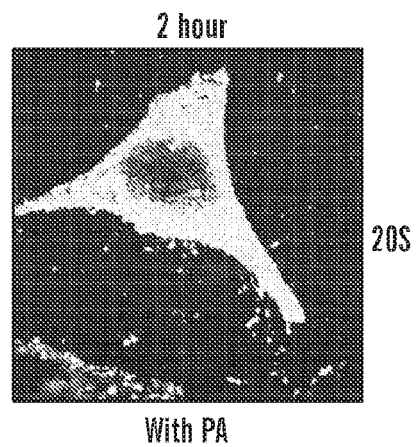
Figure 16K:
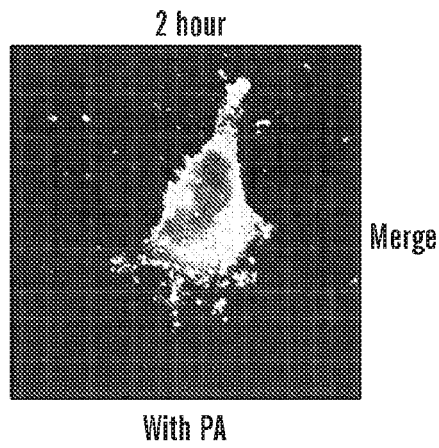
Figure 16L:
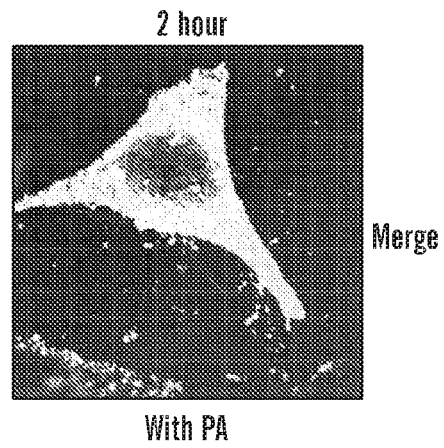

The novel fusion polypeptides of the present invention can include a single target antigen or multiple target antigens as part of a single fusion protein. A preferred fusion polypeptide includes fragments of several HIV-1 proteins, such as gag and nef (FIGS. 8, 9).

One can also create epitopes using multiple strains of an infectious virus such as with HIV. (See FIG. 9).

The novel fusion polypeptides may be part of larger multimeric molecules which may be produced recombinantly or may be synthesized chemically. Such multimers may also include the polypeptides fused or coupled to moieties other than amino acids, including lipids and carbohydrates.

Preferably, the multimeric proteins consist of multiple T cell epitopes repeated within the same molecule, either randomly, or with spacers (amino acid or otherwise) between them.

DNA sequences encoding these novel fusion proteins can readily be made. For example, the sequence encoding LFn is well known and can be modified by known techniques, such as deleting the undesired regions, such as variable loops, and to insert any additional desired coding sequences, such linker segments. The sequences encoding various target antigens are also known in the art. In addition, the codons for the various amino acid residues are known and one can readily prepare alternative coding sequences by standard techniques.

DNA sequences can be used in a range of animals to express the novel fusion protein, which can then be used for a variety of uses, including in a vaccine composition and in CMI assays, as described below.

DNA sequences encoding the novel fusion protein can be expressed in a wide variety of host/vector combinations. Vectors include chemical conjugates such as those described in WO 93/04701, which has targeting moiety (e.g. a ligand to a cellular surface receptor), and a nucleic acid binding moiety (e.g. polylysine), viral vectors (e.g. a DNA or RNA viral vector), plasmids, phage, etc. The vectors can be chromosomal, non-chromosomal or synthetic.

Useful expression vectors for eukaryotic hosts, include, for example, vectors comprising expression control sequences from SV40, bovine papilloma virus, adenovirus, adeno-associated virus, cytomegalovirus and retroviruses. Useful expression vectors for bacterial hosts include bacterial plasmids, such as those from *E. coli*, including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g. lambda.GT10 and .lambda.GT11, and other phages. Useful expression vectors for yeast cells include the 2 micron. plasmid and derivatives thereof. Useful vectors for insect cells include pVL 941.

Preferred vectors include viral vectors, fusion proteins and chemical conjugates.

Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include herpes virus vectors such as a herpes simplex I virus (HSV) vector (Geller, A. I. et al., *J. Neurochem* 64: 487, 1995; Lim, F. et al., in *DNA Cloning: Mammalian Systems*, D. Glover, Ed., Oxford Univ. Press, Oxford England, 199); Geller, A. I., *Proc. Natl. Acad. Sci. USA* 90: 7603, 1993; Geller, A. I., I *Proc Natl. Acad. Sci. USA* 87: 1149, 1990), adenovirus vectors (LeGal LaSalle et al., *Science* 259: 988, 1993; Davidson, et al., *Nat. Genet.* 3: 219, 1993; Yang, et al., *J. Virol.* 69: 2004, 1995), and adeno-associated virus vectors (Kaplitt, M. G., et al., *Nat. Genet.* 8:148, 1994). The DNA sequence is operably linked to a promoter that permits expression in the host cell. Such promoters are well known in the art and can readily be selected.

A wide variety of unicellular host cells are useful in expressing the DNA sequences of this invention. These hosts may include well known eukaryotic and prokaryotic hosts, such as strains of *E. coli, Pseudomonas, Bacillus, Streptomy-* ces, fungi, yeast, insect cells such as *Spodoptera frugiperda* (SF9), animal cells such as CHO and mouse cells, African green monkey cells such as COS 1, COS 7, BSC 1, BSC 40, and BMT 10, and human cells, as well as plant cells in tissue culture. The molecules of the present invention can be used to create a range of producer cells. This is particularly useful with certain proteins that are currently difficult to express in cells in large amounts.

The molecules comprising the novel fusion polypeptides encoded by the DNA sequences of this invention may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

Stabilized forms of these novel fusion proteins can readily be made, for example, by conjugates such as a poly(alkylene oxide) conjugate. The conjugate is preferably formed by covalently bonding the hydroxyl terminals of the poly(alkylene oxide) and a free amino group in a portion of the fusion protein that will not affect its conformation. Other art recognized methods of conjugating these materials include amide or ester linkages. Covalent linkage as well as non-covalent conjugation such as lipophilic or hydrophilic interactions can be used.

The conjugate can be comprised of non-antigenic polymeric substances such as dextran, polyvinyl pyrrolidones, polysaccharides, starches, polyvinyl alcohols, polyacryl amides or other similar substantially non-immunogenic polymers. Polyethylene glycol(PEG) is preferred. Other poly(alkylenes oxides) include monomethoxy-polyethylene glycol polypropylene glycol, block copolymers of polyethylene glycol, and polypropylene glycol and the like. The polymers can also be distally capped with C1-4 alkyls instead of monomethoxy groups. The poly(alkylene oxides) used must be soluble in liquid at room temperature. Thus, they preferably have a molecular weight from about 200 to about 20,000 daltons, more preferably about 2,000 to about 10,000 and still more preferably about 5,000.

Those of ordinary skill in the art will recognize that a large variety of possible moieties can be coupled to the resultant novel fusion proteins of the invention. See, for example, "Conjugate Vaccines", *Contributions to Microbiology and Immunology*, J. M. Cruse and R. E. Lewis, Jr (eds.), Carger Press, New York, 1989, the entire contents of which are incorporated herein by reference.

Coupling may be accomplished by any chemical reaction that will bind the two molecules so long as the novel fusion protein and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol.* 133:1335-2549, 1984; Jansen, F. K., et al., *Imm. Rev.* 62:185-216, 1982; and Vitetta et al., supra).

Preferred linkers are described in the literature. See, for example, Ramakrishnan, S., et al., Cancer Res. 44: 201-208 (1984), describing the use of MBS (M-maleimidobenzoyl-N-hydroxysuccinimide ester). See also Umemoto et al., U.S. Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The novel fusion proteins of the present invention can be used for the stable expression of proteins. For example, certain proteins are difficult to express in certain expression systems, including bacterial expression systems. Fusion to a transport factor such as LFn can stabilize certain such proteins. We have found that the transport factor is preferably 250 amino acids or less, still more preferably 150 amino acids or less, more preferably 105 amino acids or less, even more preferably 80 amino acids or less.

The novel fusion proteins of the present invention can be used to generate an immune response. For example, as a vaccine.

An exemplary pharmaceutical composition is a therapeutically effective amount of a novel fusion protein that can induce an immune reaction, thereby acting as a prophylactic immunogen, optionally included in a pharmaceutically-acceptable and compatible carrier. The term "pharmaceutically-acceptable and compatible carrier" as used herein, and described more fully below, includes (i) one or more compatible solid or liquid filler diluents or encapsulating substances that are suitable for administration to a human or other animal, and/or (ii) a system, capable of delivering the molecule to a target cell. In the present invention, the term "carrier" thus denotes an organic or inorganic ingredient, natural or synthetic, with which the molecules of the invention are combined to facilitate application. The term "therapeutically-effective amount" is that amount of the present pharmaceutical composition which produces a desired result or exerts a desired influence on the particular condition being treated. For example, the amount necessary to raise an immune reaction to provide prophylactic protection. Typically when the composition is being used as a prophylactic immunogen at least one "boost" will be administered at a periodic interval after the initial administration. Various concentrations may be used in preparing compositions incorporating the same ingredient to provide for variations in the age of the patient to be treated, the severity of the condition, the duration of the treatment and the mode of administration.

In a preferred embodiment, the novel fusion polypeptides of this invention which are also immunogenic polypeptides are incorporated into a multicomponent vaccine which can comprise other immunogenic polypeptides. A multicomponent vaccine may contain novel fusion protein(s) of the present invention to elicit T cell responses, as well as other antigens to elicit B cell responses.

In one preferred method of immunization one would prime with one novel fusion protein and then boost with a different novel fusion protein.

One can also use cocktails containing a variety of different novel fusion proteins to prime and boost with either a variety of different novel fusion proteins or with fusion proteins that contain multiple antigens (FIGS. 8, 9).

The novel fusion proteins can be used to generate a range of T cells that recognize and interact with a diverse range of antigens, for example, from different HIV strains. The DNA sequence encoding the noel fusion proteins can also be used as a subunit vaccine.

In trying to generate an immune reaction such as with a vaccine composition, an adjuvant is preferably also used. Adjuvants include but are not limited to Alum, RIBI Detox (Ribi Immunochemical), QS21 (Cambridge Biotech), and incomplete Freund's adjuvant. Alum is a preferred adjuvant. Another group of adjuvants include immune stimulators such as cytokines such as IL-12, IL-4 and costimulatory molecules such as B7. A wide range of molecules having immune stimulating effects are known including accessory molecules such as ICAM and LFA. In a preferred embodiment GM-CSF is administered to the patient before the initial immune administration. GM-CSF may be administered using a viral vector or an isolated protein in a pharmaceutical formulation. Combinations of adjuvants can be used such as CM-CSF, I CAM and LFA. While a strong immune response is typically generated to infectious disease antigens, tumor associated antigens typically generate a weaker immune response. Thus, immune stimulators such as described above are preferably used with them. As aforesaid, Alum is a preferred adjuvant.

The immune stimulatory composition of the present invention may be used advantageously with other treatment regiments. For example, the system may be used in conjunction with traditional treatment options for cancer including surgery, radiation therapy, chemotherapy and hormone therapy. For example, a breast cancer vaccine comprising a novel fusion protein of the present invention can be used in conjunction with tamoxifen citrate, which interferes with the activity of estrogen. The system may also be combined with immunotherapy, e.g. using Herceptin™ (trastuzumab), an anti-HER2 humanized monoclonal antibody developed to block the HER2 receptor; bone marrow transplantation; and peripheral blood stem cell therapy can also be used. Other preferred treatment regiments to be used in conjunction with the present composition include angiogenesis is inhibitors and cytotoxic agents.

The term "compatible", as used herein, means that the components of the pharmaceutical compositions are capable of being commingled with a small molecule, nucleic acid and/or polypeptides of the present invention, and with each other, in a manner such that does not substantially impair the desired pharmaceutical efficacy.

Doses of the pharmaceutical compositions of the invention will vary depending on the subject and upon the particular route of administration used. Dosages can range from 0.1 to 100,000 µg/kg per day, more preferably 1 to 10,000 µg/kg. Preferred doses of the compositions are preferably at least 2 µg/ml. By way of an example only, an overall dose range of from about, for example, 1 microgram to about 300 micrograms might be used for human use. This dose can be delivered at periodic intervals based upon the composition. For example on at least two separate occasions, preferably spaced apart by about 4 weeks. Other compounds might be administered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at a subsequent date, e.g., 5 months after second dose. See Product Information, *Physician's Desk Reference*, Merck Sharp & Dohme (1990), at pages 1442-43. (e.g., Hepatitis B Vaccine-type protocol); (ii) for example with other vaccines the recommended administration for children is first dose at elected date (at age 6 weeks old or older); a second dose at 4-8 weeks after first dose; a third dose at 4-8 weeks after second dose; a fourth dose at 6-12 months after third dose; a fifth dose at age 4-6 years old; and additional boosters every 10 years after last dose. See Product Information, *Physician's Desk Reference*, Merck Sharp & Dohme (1990), at pages 879 (e.g., Diphtheria, Tetanus and Pertussis-type vaccine protocols). Desired time intervals for delivery of multiple doses of a particular composition can be determined by one of ordinary skill in the art employing no more than routine experimentation.

The novel fusion proteins of the invention may also be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

The compositions include those suitable for oral, rectal, intravaginal, topical, nasal, ophthalmic or parenteral administration, all of which may be used as routes of administration using the materials of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques. Intramuscular administration is preferred.

The compositions may conveniently be presented in unit dosage form and may be prepared by any of the methods well known in the art of pharmacy. Methods typically include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the nucleic acid and/or polypeptide of the invention in liposomes or as a suspension in an aqueous liquor or non-aqueous liquid such as a syrup, an elixir, or an emulsion.

Preferred compositions suitable for parenteral administration conveniently comprise a sterile aqueous preparation of the molecule of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

To further improve the likelihood of producing a cell mediated response as provided by the invention, the amino acid sequence of polypeptides encoded by a nucleotide sequence of the present invention may be analyzed in order to identify desired portions of amino acid sequence which may be associated with receptor binding. For example, polypeptide sequences may be subjected to computer analysis to identify such sites.

Complexes that form with molecules of the present invention can be detected by appropriate assays, such as the CMI assays discussed below and by other conventional types of immunoassays.

The present invention provides assays to measure cell-mediated immune responses in vitro. Current available laboratory assays to detect CMI responses have serious shortcomings, especially when applied to large vaccine efficacy trials at various clinical settings. This is because the available equipment and technical support are minimal. As discussed above, the belief that CTL play a crucial role in controlling HIV-1 infection, many HIV-1 vaccine candidates are designed to stimulate T cell responses as well as neutralizing antibodies (1-6).

The method of the present invention for measuring T cell responses will have a significant effect on the development of all T cell dependent vaccines or immune therapies. This strategy is applicable to other field of research where CMI responses play an important role in prevention and controlling of the diseases.

In a preferred embodiment, the present invention provides use of the novel fusion polypeptides in the Elispot assay. The main advantage of the Elispot assay is that a large number of CTL responses can be evaluated effectively and efficiently in a large number of people (see for example, Lalvani et al., *J. Exp. Med.* 186:859-65 (1997)). The Elispot assay can use any standard cells, including cryopreserved PBMCs as well as CD8+ CTL cells. For example, CD8+ CTL clones from HIV-1 positive individuals.

Another preferred embodiment provides use of the novel fusion polypeptide in flow-based intracellular cytokine assays. Flow cytometry-based assays detect the intracellular accumulation of cytokines after in vitro stimulation of antigen specific T cells. CTLs are stimulated with antigens and incubated with brefeldin A, which inhibits protein transport and allows intracellular accumulation of newly synthesized proteins such as cytokines. Surface markers (CD8, CD3) and intracellular staining of IFN-γ and CD69 allows detection and quantitation of specific cell populations against antigenic epitopes in the context of uncharacterized MHC backgrounds.

The CMI assays using the novel fusion polypeptides of the present invention can be used to evaluate cellular immune responses against a broad array of viral, bacterial, and tumor antigens. The assays can be used in either evaluating vaccine efficacy or in arresting the statues of infection by infectious pathogens.

The CMI assays using the novel fusion polypeptides of the present invention can also be used as early diagnostic kits to detect cancer antigens.

The present invention also provides a kit for detecting CMI responses. One preferred kit contains novel fusion proteins in these tubes, wells, etc. The kit preferably contains viral or tumor containing reagents to detect CMI responses in vitro. Preferably, the kit contains an apparatus for removing a biological specimen such as blood. In a preferred embodiment, the kit will contain instructions for detecting CMI responses. Preferably, the kit contains the novel fusion protein in a lyophilized form.

A preferred kit includes the novel fusion protein lyophilized and coated onto the inside of a tube used for the collection of blood. This allows blood to be drawn from an individual directly into the tube, incubated for several hours (for example, 4 hours), and then fixed. Such fixed samples are stable for use in CMI assays for extended periods of time (for example, two weeks). The kit is particularly useful for correcting samples in the field, for example, during vaccine efficacy trials, which typically occur in remote locations. Similarly, other preferred embodiments include the lyophilized protein coated onto any surface, such as a dish, a well, or a tube, which is amenable to adding a small volume of a biological specimen. Preferred biological specimens include blood, urine, sputum, stool, supernatant from cerebrospinal fluid, and cell samples.

In a specific example, LFn fusion proteins such as those described above which can contain only the carboxy portion of LFn, can in the absence of PA sensitize CTL target cells in a MHC-I restricted manner. In this novel method of presenting exogenous protein antigens to the MHC-I pathway, the cytosolic delivery of the antigens relies on the functional transportation associated with intracellular antigen processing, without resorting to live viral or bacterial vectors. These LFn fragments are an example of a new class of proteins that enters the MHC-I pathway from the cytosol. The fact that for example, LFn can deliver HIV-1 antigens into cytosol in the absence of PA is in contrary to the current hypothesis of how anthrax lethal toxin works (32). In the normal case, LF (anthrax lethal factor) is dependent on PA to exert its toxic effect and possibly the toxic domain of LF possess unknown functions that prevent cell entry.

Additionally, fusion proteins such as LFn-HIV can be used as a tool to refine and simplify the methods for detecting T cell responses in vaccine trials. This method is also useful for studies of other intracellular viral or bacterial diseases, such as viral hepatitis, TB, and malaria. The present invention can circumvent the need for using live recombinant vaccinia viruses in the current CMI assays. It also carries several advantages over using overlapping synthetic peptides, which are not only expensive, but that their theoretical coverage of different populations with HLA-I diversity remains unproven. The novel antigen delivery provides simplified CMI assays that are widely applicable to field use. Furthermore, these LFn fusion proteins are easily produced in *E. coli*, purified in relatively simple procedures, and are stable.

All of the novel fusion polypeptides provided by this invention, and the DNA sequences encoding them, are substantially free of a *B. anthracis* protective antigen or fragments thereof, and thus may be safely used in a variety of applications without the risk of unintentional damage to the host. Accordingly, the novel fusion polypeptides of this invention are particularly advantageous in compositions and methods for generating a broad range of cell-mediated responses to target antigens.

The following Examples serve to illustrate the present invention, and are not intended to limit the invention in any manner.

EXAMPLE 1

Materials and Methods

LFn-HIV Fusion Proteins

The DNA fragment encoding env gp120, gag p24 from HIV-HXB were amplified by PCR, cloned into the LFn expression plasmid pET15bLFn, and sequenced to verify the inframe fusion between the LFn and the HIV coding sequence. The Nef coding sequence was amplified from HIV-ELI. The protein expression vector for LFn and its fusion derivatives is the pET15b plasmid (Novagen; Madison, Wis.). The main features of this vector system include an inducible T7 promoter, an internal His-Tag for protein purification, and multiple cloning sites. The recombinant LFn is expressed in *E. coli* as an intracellular soluble protein with 6 tandem histidine residues at its N-terminal end (14). Bacteria were grown in a ten-liter Bioflow 2000 bench top bioreactor (New Brunswick Scientific, NJ). Purification of the His-tagged proteins was conducted using a commercial kit according to the manufacturer's protocol (Novagen). Fragments of LFn can be made by modifying the LFn coding region by known techniques.

Reagents

Synthetic peptides were synthesized on an Applied Biosystems Peptide

Synthesizer (Model 430A). Recombinant vaccinia viruses used were vAbT 141 (Gag), vAbT 299 (Env), and Nef (15) with NYCH as control vaccinia vector. Brefeldin A, cytochalasin B and chloroquine (Sigma, St Louis, Mo.) were added to cell culture for 2 hours and washed twice before adding back to the cells. Antibodies for flow analysis were obtained from Becton-Dickinson (San Jose, Calif.)

Flow-Based Intracellular Cytokine Staining

Cryopreserved PBMCs were incubated overnight with LFN-HIV (30 ug/ml), recombinant vaccinia vectors (MOI 3-5) or peptides (10 ug/ml) at 37° C. in 5% $CO_2$. Autologous B-LCLs were incubated overnight with optimal peptides (10 ug/ml), LFn-HIV (10 ug/ml) or recombinant vaccinia viruses (MOI 3-5), washed twice and added to effector cells at E:T ratio of 10:1 in the presence of co-stimulatory anti-CD28 and anti-CD49d (1 ug/ml, Becton-Dickinson, San Jose, Calif. Brefeldin A (10 ul of 1 mg/ml) was subsequently added and the cell culture was incubated at 37° C. for 6 hours and stained with saturating solution of isotype controls (IgG1 for APC, PE, PerCP and IgG2b for FITC) or allophycocyanin (APC)—labeled CD3 monoclonal antibody (Mab), phycoerythrin (PE)-labeled anti-CD8 Mab (Becton Dickinson). After incubating in dark at 4° C. for 20 minutes, the cells were washed twice with FACS wash. 100 ul of reagent A (Fix and Perm kit, Caltag Laboratories, Austria) was added and after incubating in dark at room temperature (RT) for 20 minutes, the cells were washed twice with FACS wash. 100 ul of reagent B (Fix and Perm kit) was then added and cells were incubated at RT for 5 minutes. After adding FITC-IFN gamma and peridinin chlorophyll protein (PerCP)-conjugated CD69 Mab (CD69 perCP) antibody and incubating in dark at 4° C., the cells were washed twice with FACS wash and analyzed on Becton Dickinson FACScalibur flow cytometer using the Cell Quest software.

Samples were analyzed with four colors staining using the FACSCalibur Flow Cytometer (Becton Dickinson) and Cellquest software (Becton Dickinson). Negative and positive controls used were unstimulated cells as well as cells stimulated, respectively, with mitogen phematohemaglutinin PHA (0.25 ug/ml, Murex Biotech).

Cell Lines and Culture Conditions.

Autologous Epstein-Barr virus (EBV)-transformed B lymphoblastoid as well as T1 and T2 (HLA-B60) cell lines were used as antigen presenting cells (APCs). Target cells were pulsed with the appropriate index peptides or LFn-HIV constructs or infected overnight with recombinant vaccinia viruses. AC13 (HLA B14 restricted p24 [DRFYKTLRA] (SEQ ID NO: 4)) and KM (HLV B60-restricted Nef [KEKG-GLEGL] (SEQ ID NO: 5)) are Gag and Nef-specific clones (respectively) and AC2 (HLA B44 restricted gp120 [AENL-WVTVY](SEQ ID NO: 6)). All were obtained from HIV infected individuals whose CTL responses are well characterized (Rosenberg, personal communication) and the Env-specific clone (SP 511) was generated from a seropositive Ugandan (16). PMBCs used in the Elispot study were HIV-1 infected individuals from Senegal and Uganda (15,16). To investigate the effect of brefeldin A, cytochalasin B or chloroquine on MHC class I restricted presentation of LFn-HIV, APCs were labeled with the protein constructs, cultured in RPMI 1640m 10% FCS and cocultured with respective reagents for one hour, then washed and tested in the standard chromium release assay.

Elispot

Elispot assay was performed on cryopreserved PBMCs. 96-well nitrocellulose plates (Millititer, Millipore Corp., Bedford, Mass.) were pre-coated overnight in 4° C. with 0.5 mg/ml of monoclonal antibody 1-D1K (Mabtech, Stockholm, Sweden). The plates were then washed 6× with phosphate-buffered saline (PBS) and PBMCs were added at 50,000 cells/well and 25,000 cells/well in duplicate wells, respectively. The plates were incubated overnight at 37° C. in 5% CO2 and biotinylated monoclonal antibody anti-IFN-Mab (Mabtech) was then added at 0.5 mg/ml for 100 minutes followed by streptavidin-ALP (Mabtech) for 1 hour at room temperature. The plates were washed three times with PBS and 5-bromo-4-chloro-3-indolyl phosphate and nitro blue (Sigma) added to develop the reaction. Tap water was added to stop the reaction after 15 minutes. Individual cytokine-producing cells were detected as dark spots, which were visualized and quantitated as SFC/well (spot forming colony/well). CTL frequency (CTLp) was calculated from the number of spots subtracted from the control wells and averaged from the four wells. The final CTLp was reported as the average frequency per $10^6$ cells. Responses were considered positive if the SFCs were at least twice that of control. Background SFC was on average less than 15/well.

Chromium Release Assay:

CD8+ CTL clones were stimulated with anti CD3 monoclonal antibody (12F6) in the presence of recombinant IL-2 and tested for activity within seven days. Target cells included autologous B-LCL or HLA-matched APCs infected with recombinant vaccinia virus (multiplicity of infection 3 to 5) expressing HIV-1 gene products or with LFn proteins (5 to 30 ug/ml) overnight and labeled with radioactive chromium ($^{51}$Cr). Effector:target cell ratio (E:T) was 10:1 in a final volume of 200 ul with all assays performed in duplicate wells. Supernatant fluid was harvested after 4 hours and the percent specific lysis was determined from the formula: 100×[(experimental release-spontaneous release)/(maximum release-spontaneous release)]. HIV-specific CTL activity was defined as 10% above background/control. Spontaneous release was <30% of maximal release for all assays.

LFn-HIV Mediates HIV-1 Antigen Entry and Processing without PA:

To assess the ability of LFn-HIV to associate with MHC-I molecule on cell surface, lymphoblastoid B cell lines (B-LCL) were sensitized with LFn-HIV in the presence or absence of PA and tested in a standard chromium release assay using several well characterized HIV-specific CTL clones (FIG. 3). We found that CTL recognized target cells sensitized with LFn-HIV comparably in the presence or absence of PA. Lysis level was dose-dependent and achieved to levels comparable to positive controls where B-LCLs were infected with recombinant vaccinia viruses expressing the same HIV antigens. HIV-specific CTL activity was evident only when targets had a longer incubation period with LFn-HIV (8 hours vs 1 hour) (data not shown), suggesting a delay in the appearance of surface antigen and the requirement for intracellular processing.

LFn-HIV is Presented in the Classical MHC-I Pathway

We next verified that LFn-HIV was presented by the classical MHC-I pathway, by demonstrating that the recognition of these constructs by CTLs was HLA-I restricted (FIG. 4). Two Nef- (KM) and Gag-specific (AC13) clones that are HLA B60- and B14-restricted, respectively, were tested with HLA matched and mismatched targets presenting LFn-Nef or LFn-p24. Only HLA-matched targets demonstrated significant lysis, confirming the MHC-I presentation of LFn-HIV.

We further examined the potential mechanism of uptake and processing of LFn-HIV. To determine whether the internalization of LFn-HIV at the surface was actively processed, we pre-incubated B-LCL with 100 uM of cytochalasin B (17,18), a phagocytosis inhibitor before adding LFn-HIV antigens. CTL recognition was abrogated in the presence of cytochalasin B, suggesting an endocytosis-mediated internalization process.

If exogenous LFn fusion protein was introduced and subsequently processed in the cytosol, TAP proteins (Transporter associated with antigen processing) would be required for the transport of peptides into the ER lumen for binding to MHC-I (19-21). To evaluate the requirement for antigenic processing after endocytosis, we tested the ability of LFn-HIV fusion proteins to sensitize the B60-expressing cell lines T1 and T2 to lysis by CTL. T2 cell (22-24) is a derivative of T1 cells lacking the function of TAP, which transports peptides from the proteosome to the ER lumen for binding to MHC-I (19, 20). Recognition was abrogated in T2 cells (FIG. 4B), indicating the need for epitope transport after processing. Recognition of this TAP deficient target by the same clone was maintained if the cells were pulsed with the optimal epitope peptide directly to the surface "empty" MHC-I molecule, bypassing the requirement for intracellular processing.

To further verify the mechanism of exogenous protein entry into the MHC class I pathway, target cells were treated with brefeldin A, which inhibits exocytosis of proteins from the ER and Golgi complexes and prevents newly assembled peptide-MHC complexes from reaching the cell surface (25). The addition of brefeldin A before presenting the target cells with LFn-HIV effectively blocks recognition by CTLs (FIG. 5). This finding, together with the earlier demonstration for HLA restriction and TAP requirement, confirms that LFn-HIV was processed and presented by B-LCL in a MHC class I pathway.

Processing of LFn-HIV is Chloroquine Insensitive

The presentation of many exogenous antigens on MHC-I molecule involves proteolysis in the endocytic compartment (26-28) and the peptides subsequently gain access to the cytosol where it enters the MHC class I pathway. To investigate whether LFn mediated antigen presentation requires proteolysis in acidic vesicles, we treated the B-LCL with chloroquine during exposure to LFn-HIV (FIG. 5). It is known that chloroquine raises the pH in the endosomal and lysososmal compartments thus inhibiting protein hydrolysis by cathepsins, which require an acidic environment for activity (29,30). Our finding suggested that phagosomes with leaky properties are not requisite for the entry of LFn-HIV into the cytosol.

The addition of either cytochalasin B, brefeldin A or chloroquine did not affect recognition and lysis of target cells if targets were pulsed with the optimal 8-mer epitopes at the surface, demonstrating that these reagents did not affect CTL function nor target viability (FIG. 5).

Comparing LFn-HIV with Recombinant Vaccinia Virus in Different CMI Assays

Having demonstrated the ability of LFn-HIV to present CTL epitopes with MHC-I molecules at the cell surface, we proceeded to test the applicability of the LFn fusion proteins in various CMI assays, including the enzyme linked spot (Elispot) assay and flow-based intracellular interferon assay. These assays provide simpler and more rapid estimate of T cell responses and theoretically better suited for large clinical testing, especially in context of vaccine studies. The main advantage of the Elispot assay is that the HIV-specific CTL response can be evaluated effectively and efficiently in large number of people (31). Currently various antigen stimuli are used in this assay, including recombinant vaccinia viruses expressing HIV antigens or overlapping synthetic peptides. Cryopreserved PBMCs as well as CD8+ CTL clones from several HIV-1 positive individuals were tested in the Elispot assay, using LFn-p24, LFn-Nef or LFn-gp120 in parallel with recombinant vaccinia viruses expressing the same antigens. Comparable spot forming colonies were observed with LFn-HIV and in some instances, less background spots was evident when compared to that with recombinant vaccinia virus (FIG. 6).

Flow cytometry-based assay detects the intracellular accumulation of cytokines after in vitro stimulation of antigen-specific T cells. CTLs are stimulated with antigens and incubated with brefeldin A, which inhibits protein transport and allow intracellular accumulation of newly synthesized cytokines such as IFN-γ. Surface markers (CD8, CD3) and intracellular staining of IFN-γ and CD69 allows detection of and quantification of specific T cell population against antigenic epitopes in the context of uncharacterized HLA-I backgrounds. A Nef-specific clone (KM) was stimulated with LFn-Nef and subsequently evaluated for intracellular production of the interferon by flow analysis (FIG. 7A). Nef-specific response was detected with LFn-Nef as well as recombinant vaccinia virus expressing Nef in a cell population that is CD8+. Freshly isolated, unstimulated PBMCs from an individual (AC2) with known gp120 epitope was sensitized with LFn-Env as well as with recombinant vaccinia virus expressing Env (rVV-Env). The percentage of intracellular IFN-γ in the CD8+ cell population was higher in cells exposed to LFn-Env compared to those incubated with rVV-Env (FIG. 7B).

EXAMPLE 2

LFn fusion proteins in the absence of PA are also capable of sensitizing CTL target cells in a MHC-I restricted manner. This cytosolic delivery of LFn fusion proteins relies on functional transportation associated with intracellular antigen processing inside an antigen-presenting cell (Cao H, Agrawal D, Kushner N, Touzjian N, Essex M, and Lu Y. *J. Infect. Dis.* 185:244-251 (2002)). We have now demonstrated that Green Florescence Protein (GFP) fused with LFn can enter into cells in the absence of PA. We further show that this PA-independent LFn delivery of exogenous GFP appears to be associated with cellular proteosome, which is consistent with the previous observation.

Construction and Purification of LFn-GFP and GFP

LFn-GFP fusion protein was constructed by insertion of the GFP open reading frame from pEGFP-C1 (Clontech) into the LFn expression vector described in previous studies (Lu, Y., R. et al., *Proc. Natl. Acad. Sci. USA* 97:8027-32 (2000)). The fusion protein is soluble in bacterial cell extract and can be purified in one step affinity chromatography. The purified fusion protein has a molecular weight of approximately 55 kD and its solution has a bright green color (data not shown). In order to have an appropriate control for the experiments, GFP alone was constructed into the same bacterial expression vector, pET15b, so that the only difference in the expression, purification, and use of GFP and LFn-GFP is the lack of the LFn sequences in GFP.

LFn-GFP enters CHO Cells Whereas GFP Cannot

CHO cells were cultured in collagen treated chamber slides to reach 80% confluence and were then incubated with purified LFn-GFP for one or two hours, followed by washing extensively with PBS and PBS plus proteases to remove membrane bound proteins. The cells were then stained with the anti-transferrin antibodies and fixed with paraformaldehyde. The slides were examined by confocal microscopy for green color (GFP) and red color (anti-transferrin), respectively. A third image is presented for each field by superexpose the green image with the red image of the same cells. Consequently, a yellow spot indicts that the GFP may be in the same spot with the transferrin protein, thus providing a reference to the location of GFP inside the cells. As shown in FIG. 10, a significant number of green spots were visible in cells treated with LFn-GFP for one hour, suggesting the LFn-GFP can indeed enter into cells. Under the exactly same experimental conditions, GFP-treated cells showed few green spots (FIG. 11).

Location of LFn-GFP Inside Treated-Cells

Using the identical experimental procedures described above for FIGS. 10-11, we substituted the anti-transferrin antibodies with an anti-lysosome antibody (FIG. 12), an anti-endosome antibody (FIG. 13), an anti-Golgi antibody (FIG. 14), and an anti-proteosome antibody (FIG. 15), respectively. By comparing these different images, the super-exposed images that have the most yellow spots are those shown in FIG. 15 in which the green spots representing the intracellular LFn-GFP overlap significantly with the red spots representing cellular proteosome.

The Presence of PA does not Enhance the Cellular Intake of LFn-GFP

We further examined if the presence of PA would enhance the intake of LFn-GFP under the experimental conditions used for FIGS. 10-15. As shown in FIG. 16, adding PA did not increase the number of green spots inside cells in comparison with those in the absence of PA. Moreover, it seems that the presence of PA might have reduced the amount of yellow spots. Apparently, it is likely that under these conditions these yellow spots still represent the PA-independent entry of LFn-GFP.

EXAMPLE 3

Deletion of the N-Terminal Half of LFn, and the Adjuvant Effect of Alum on LFn Immunization Additional animal immunization data demonstrates that the N-terminal half of LFn, which contains the PA binding domain, can be deleted with no negative effect on the antigen delivery. Quite unexpectedly, we found that the addition of Alum could significantly enhance the CTL induction by the LFn fusion proteins.

Despite many unsuccessful attempts in the past two years, we have been unable to show that LFn-p24 in the presence of PA could stimulate CTL in immunized BALB/c mice. Previous studies have shown that LFn fusion proteins such as LFn-V3, LFn-LLO, and LFn-OVA are capable of stimulating specific CTL in mice (Lu, Y., et al. *Proc. Natl. Acad. Sci. USA* 97:8027-32 (2000); Ballard, J. D. et al., *Proc. Natl. Acad. Sci. USA* 93, 12531-12534 (1996); Ballard, J. D., et al., *Infect. Immun.* 66, 615-619 (1998)). These fusion proteins carry only 12 to 33 amino acids, whereas LFn-p24 carries about 230 amino acids. Thus the size of the inserted antigens may make the difference. We decided to test if adding immune adjuvants could improve the immunogenicity of LFn-p24. Among the reagents we tested, which include recombinant IL2, Ig-IL2, CpG, Alum, and others, Alum unexpectedly showed the best adjuvant activity. It is widely believed that certain experimental adjuvants, such as QS21 and PCPP can enhance cell-mediated immune responses, whereas Alum actually inhibits the CTL induction (Schiembeck, R., et al., *J. Immunol.* 152: 1110-1119 (1994); Barouch, D. H. et al, *Science* 290:486 (2000); Davis, H. L. et al., *J. Immunol.* 160:870-876 (1998); Payne, L. G. et al., *Dev. Biol. Stand.* 92:79-87 (1998)).

Figure 17:
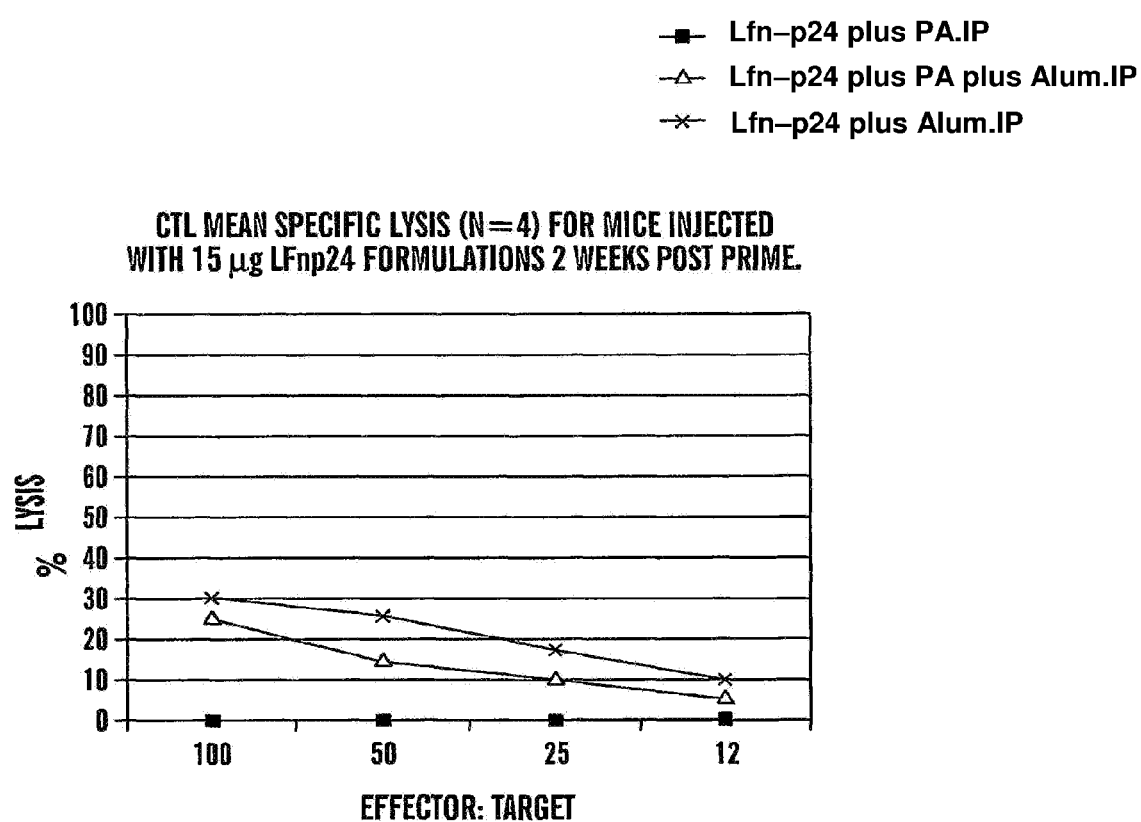
FIG. 17 Three groups of BALB/c mice, four in each group, were immunized i.p. with different antigen formulations, respectively (15 μg LFn-p24 plus 4 μg PA, 15 μg LFn-p24 plus 4 μg PA plus Alum, 15 LFn-p24 only plus Alum). At one-week post the immunization, splenic mononuclear cells from immunized BALB/c mice were used as the source of CTL. The CTL in the splenic cultures were activated in vitro by culturing with gamma-irradiated and peptide-pulsed BALB/c splenocytes from un-immunized animals. After 6 days of culture in a 37° C. $CO_2$ incubator, mature CTL (effector cells) were tested for their ability to lyse either $^{51}$Cr-labeled P20 peptide-pulsed P815 cells (positive targets) or $^{51}$Cr-labeled medium-pulsed cells (negative targets). The percent lysis shown were subtracted from the background lysis of negative targets and presented as the average of each group.

In FIG. 17, three groups of BALB/c mice, four in each group, were immunized i.p. with different antigen formulations, respectively (15 ug LFn-p24 plus 4 ug PA, 15 ug LFn-p24 plus 4 ug PA plus Alum, 15 LFn-p24 only plus Alum). At one-week post the immunization, splenic mononuclear cells from immunized BALB/c mice were used as the source of CTL. The CTL in the splenic cultures were activated in vitro by culturing with gamma-irradiated and peptide-pulsed BALB/c splenocytes from un-immunized animals. After 6 days of culture in a 37° C. $CO_2$ incubator, mature CTL (effector cells) were tested for their ability to lyse either $^{51}$Cr-labeled P20 peptide-pulsed P815 cells (positive targets) or $^{51}$Cr-labeled medium-pulsed cells (negative targets). The percent lysis shown were subtracted from the background lysis of negative targets and presented as the average of each group.

As shown in FIG. 17, with the addition of Alum, we were able to show that LFn-p24 can stimulate specific CTL in immunized mice in the presence or absence of PA. These results further demonstrate that the presence of PA is not required for the antigen delivery in vivo.

Figure 3A:
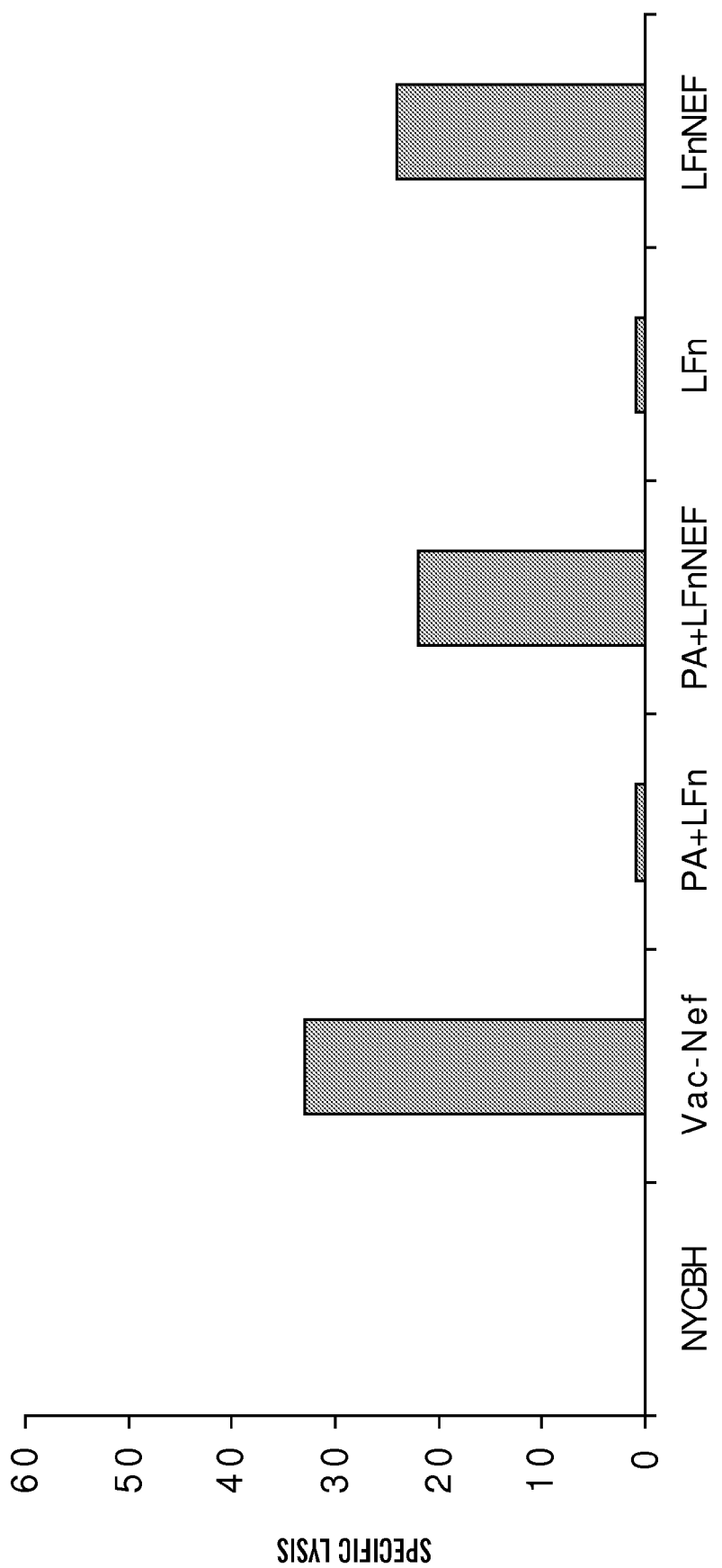
FIGS. 3A-B are graphs that show that LFn presentation of targets is PA-independent. Well characterized CTL clones were tested for activity in a standard chromium release assay at effector to target (E:T) 10:1. Targets were HLA-matched EBV-transformed cell lines that were sensitized overnight with LFN in the presence or absence of PA. Controls used were recombinant vaccinia vectors (NYCBH for control and rVV-Nef or Env peptide for appropriate clone).
Figure 3B:
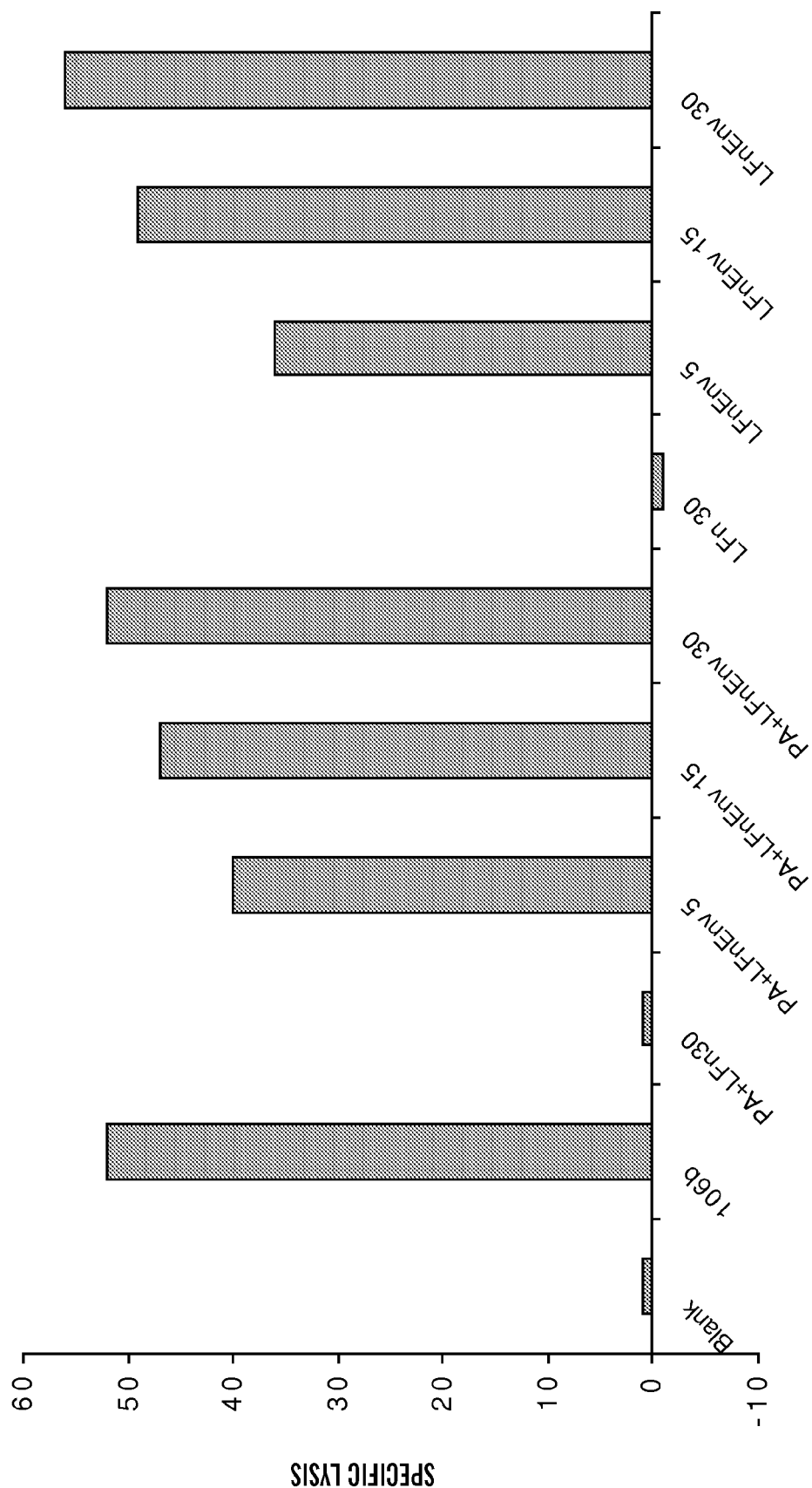
Figure 4A:
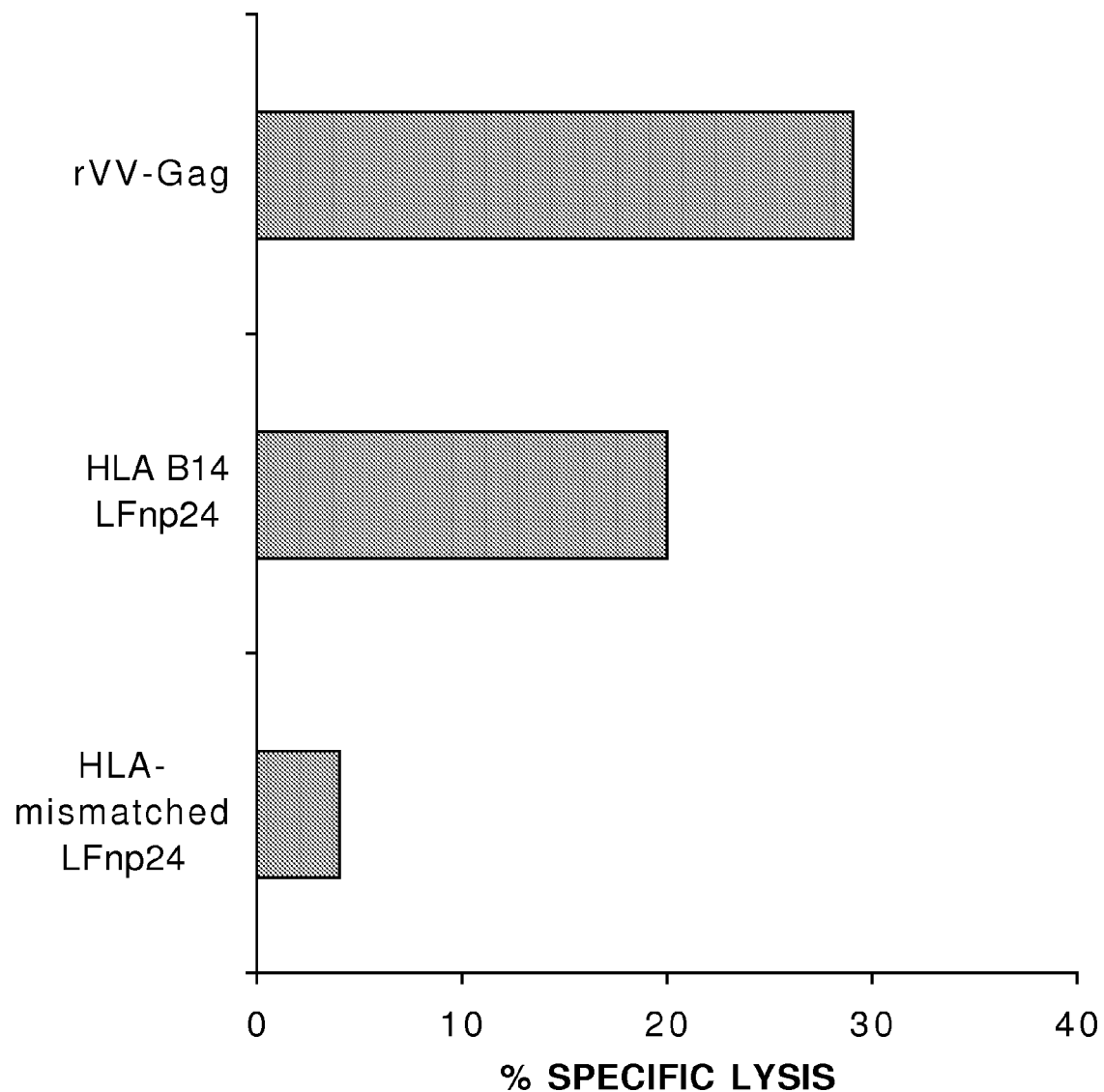
FIGS. 4A-B are graphs that show that LFn-HIV recognition is HLA-restricted. 4A shows HLA-B14 restricted Gag clone (AC13) was tested for activity using HLA matched and mismatched B-LCL sensitized with LFn-p24 and tested in standard chromium release assay. Rvv-Gag was used as control. 2B shows HLA-restriction for B60 Nef clone (KM) was demonstrated using HLA matched and mismatched targets sensitized with LFnNef. TAP-deficient (T2), HLA-B60 target cells were sensitized with LFN-Nef and the optimal Nef peptide and tested for lysis. Lack of activity with T2 LFnNef target cells suggests requirement for proteasome processing. All clones were used at E:T 10:1 and lysis level substracted from those of background controls. NYCBH was used for recombinant vaccinia virus control and LFn alone for LFnP24 and LFnNef. Positive control included Nef peptide 180 and recombinant vaccinia vector Gag (rvv-Gag).
Figure 4B:
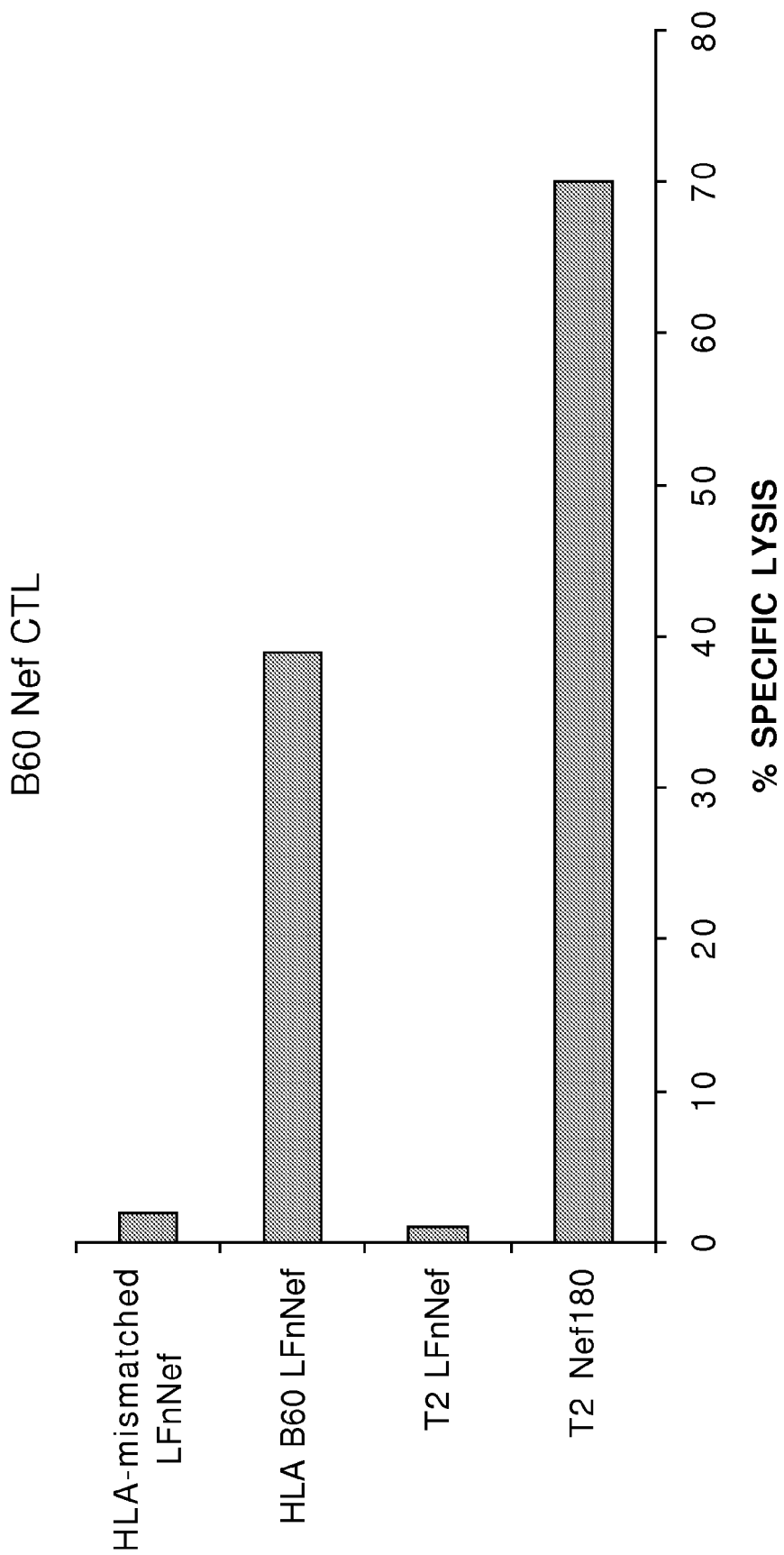
Figure 5A:
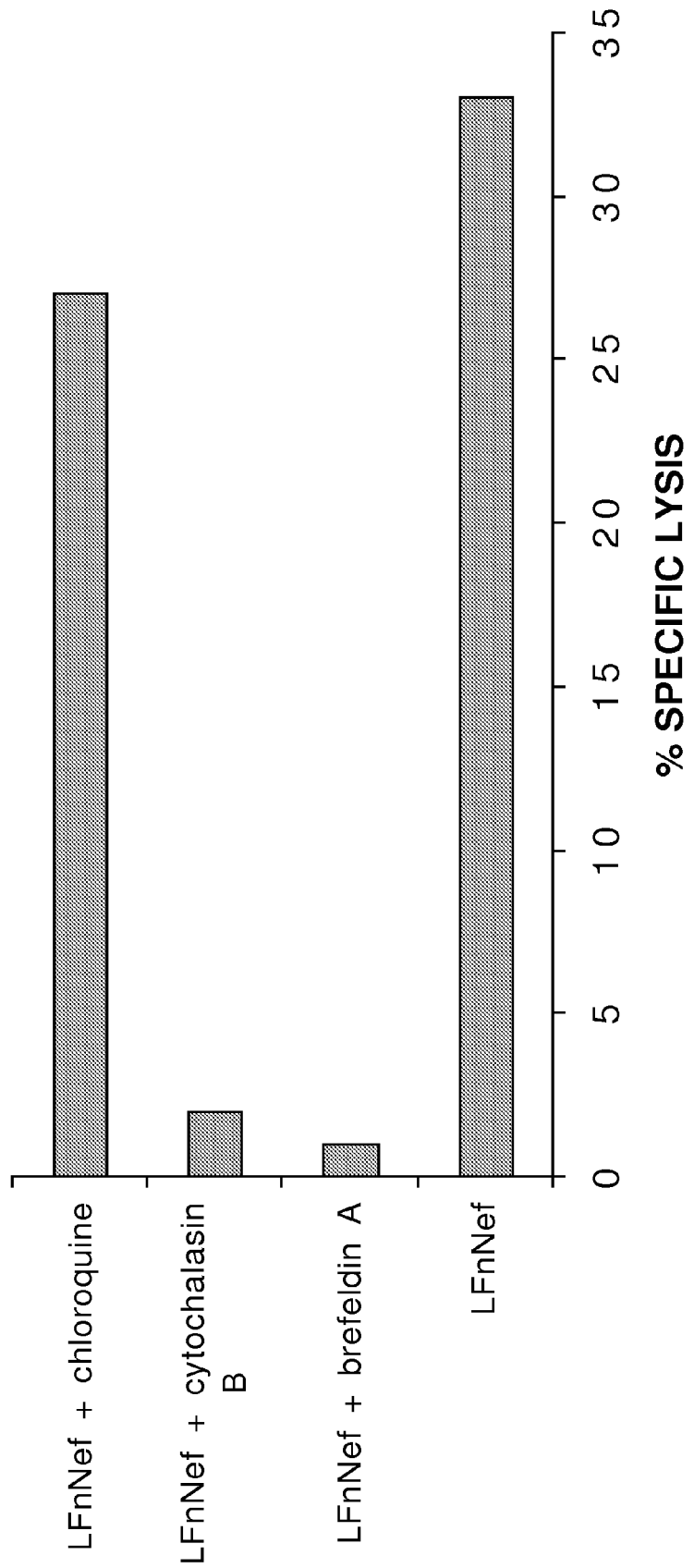
FIGS. 5A-B are graphs that show the internalization and processing of LFn-HIV. 5A shows Nef-specific clone (KM) lysis of HLA-matched target cells sensitized with LFnNef in the presence of brefeldin A, cytochalasin B and chloroquine compared to LFnNef alone. Co-incubation with cytochalasin B and brefeldin A abrogated the recognition by a Nef-specific clone but not with chloroquine. 5B shows activity of the same Nef clone with target infected overnight with recombinant vaccinia virus expressing Nef or sensitized with the optimal epitope peptide Nef 180 alone or in the presence of chloroquine, cytochalasin B or brefeldin A. No significant decrease in activity was seen when target cells and CTL clone were incubated in the presence of cytochalasin B, chloroquine or brefeldin A. Lysis levels shown are substracted from background lysis which were less than 10%.
Figure 5B:
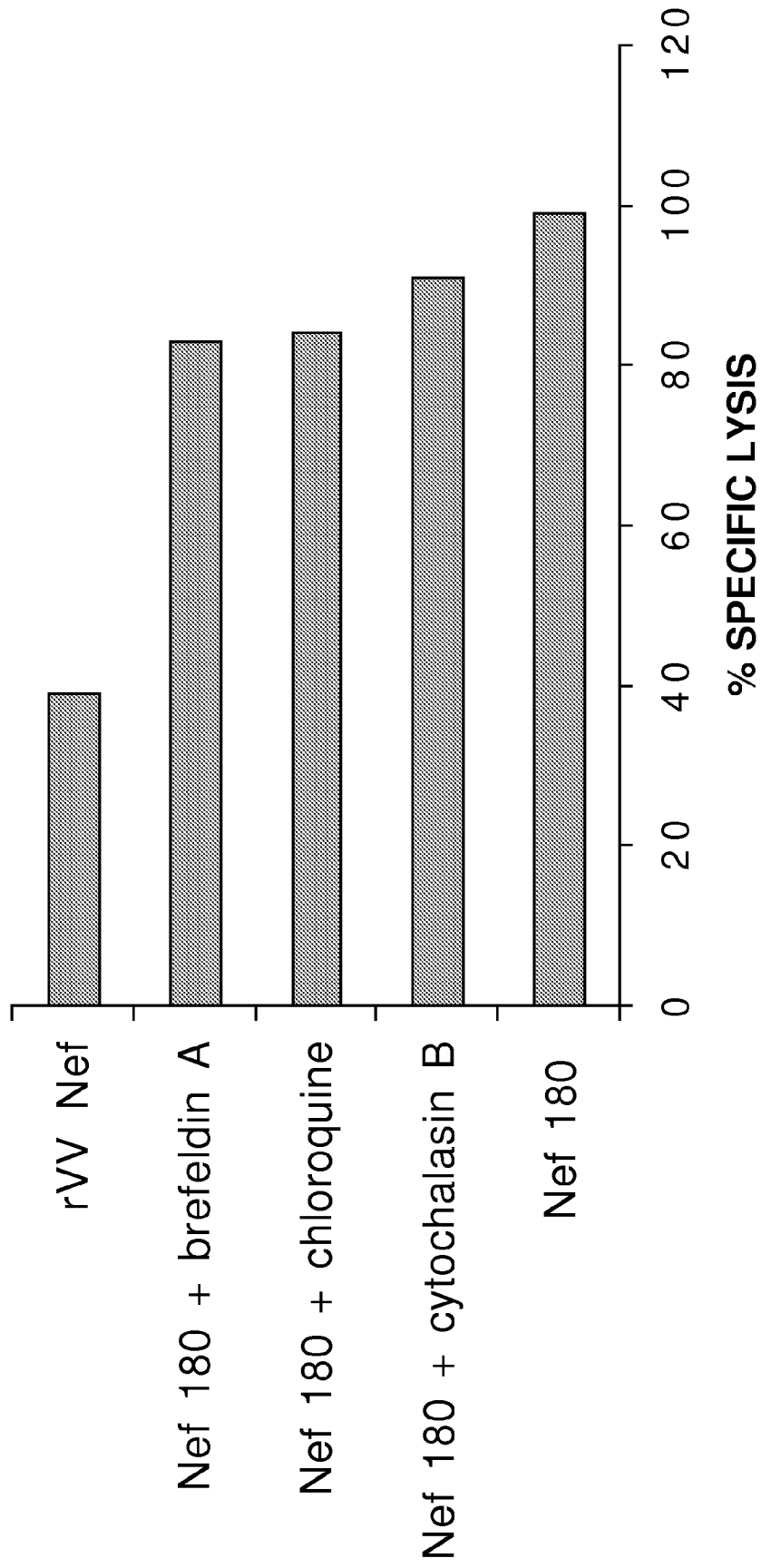
Figure 6A:
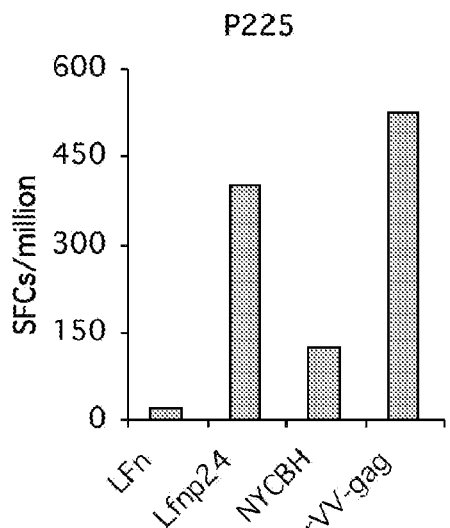
FIG. 6 are graphs that show LFn-HIV expression in the Elispot assay. Cryopreserved PBMCs from HIV-1 infected individuals with known HIV-specific CTL activity or epitopes were used in the Elispot assay using recombinant vaccinia viruses, or LFn-HIV. LFn alone and NYCBH were used as control. Duplicate wells were used at 100K cell/well. Results are reported as SFC/million (spot forming cells per million).
Figure 6B:
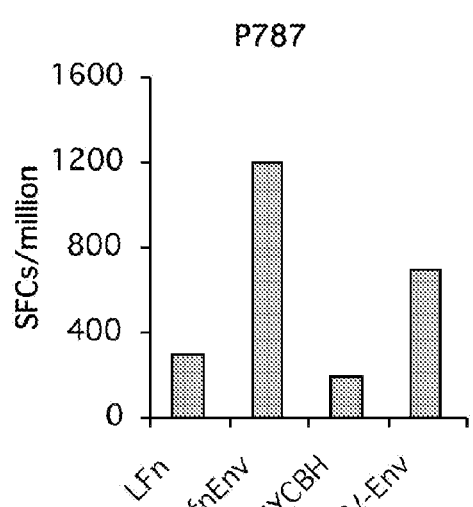
Figure 6C:
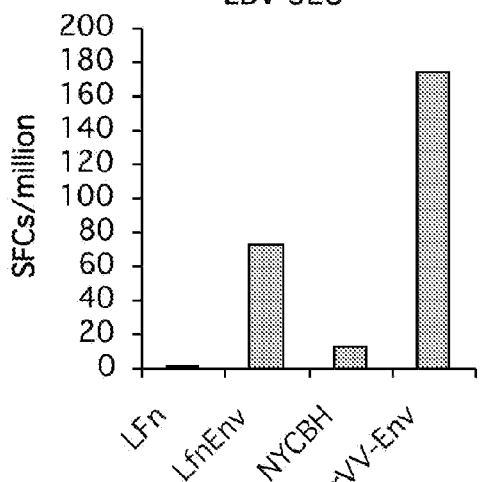
Figure 6D:
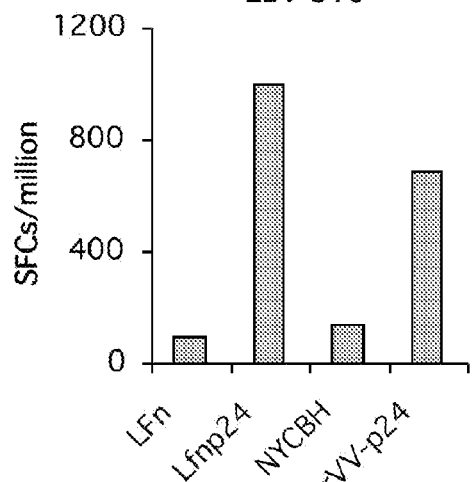
Figure 6E:
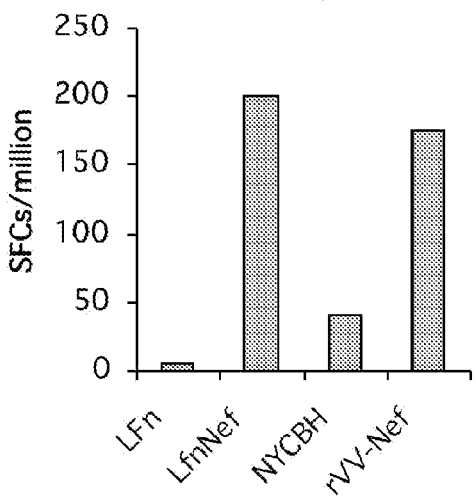

LFn Fusion Proteins where the N-Terminal Half of LFn has been Deleted are Still Active In an effort to confirm that LFn-p24 was able to elicit CTL in mice in the absence of PA, we constructed a mutated LFn fusion protein (MLFn-p24) in which 1-149 amino acids of the N-terminal of LFn was deleted to abolish its ability to bind PA. The mutated LFn (MLFn), with the deletion of 1-149 N-terminal amino acids from LFn (LFn is 1-255 amino acids)

results in a C-terminal amino acid fragment of LFn termed herein as Fragment 3 (SEQ ID NO: 3) (FIG. 3C). We confirmed this by using an experimental method specially designed to test PA-dependent membrane translocation. In brief, trypsin-nicked PA was incubated with CHO-K1 cells for 2 hours at 4° C. The cells were then washed with cold PBS and incubated with $^{35}$S-labeled LFn-NG or LFn-ENV for 2 hours at 4° C. The cells were washed extensively and exposed to MES/gluconate buffer (pH 4.8) at 37° C. for 2 minutes. Pronase E or buffer was then added to digest surface bound LFn fusion proteins that had not been internalized. The cells were then washed again, lysed, and counted. The percentage of the protein translocated by PA was calculated according the following formula. The ratio=100×(counts in the presence of PA and the Pronase treated cells−counts in the absence of PA and the Pronase treated cells)/(counts in the presence of PA and in mock treated cells−counts in the absence of PA and the mock treated cells). In this particular assay, PA translocated as high as 72% of the membrane bound LFn into the cells, whereas the amount of the MLFn translocated by PA was undetectable.

Figure 18:
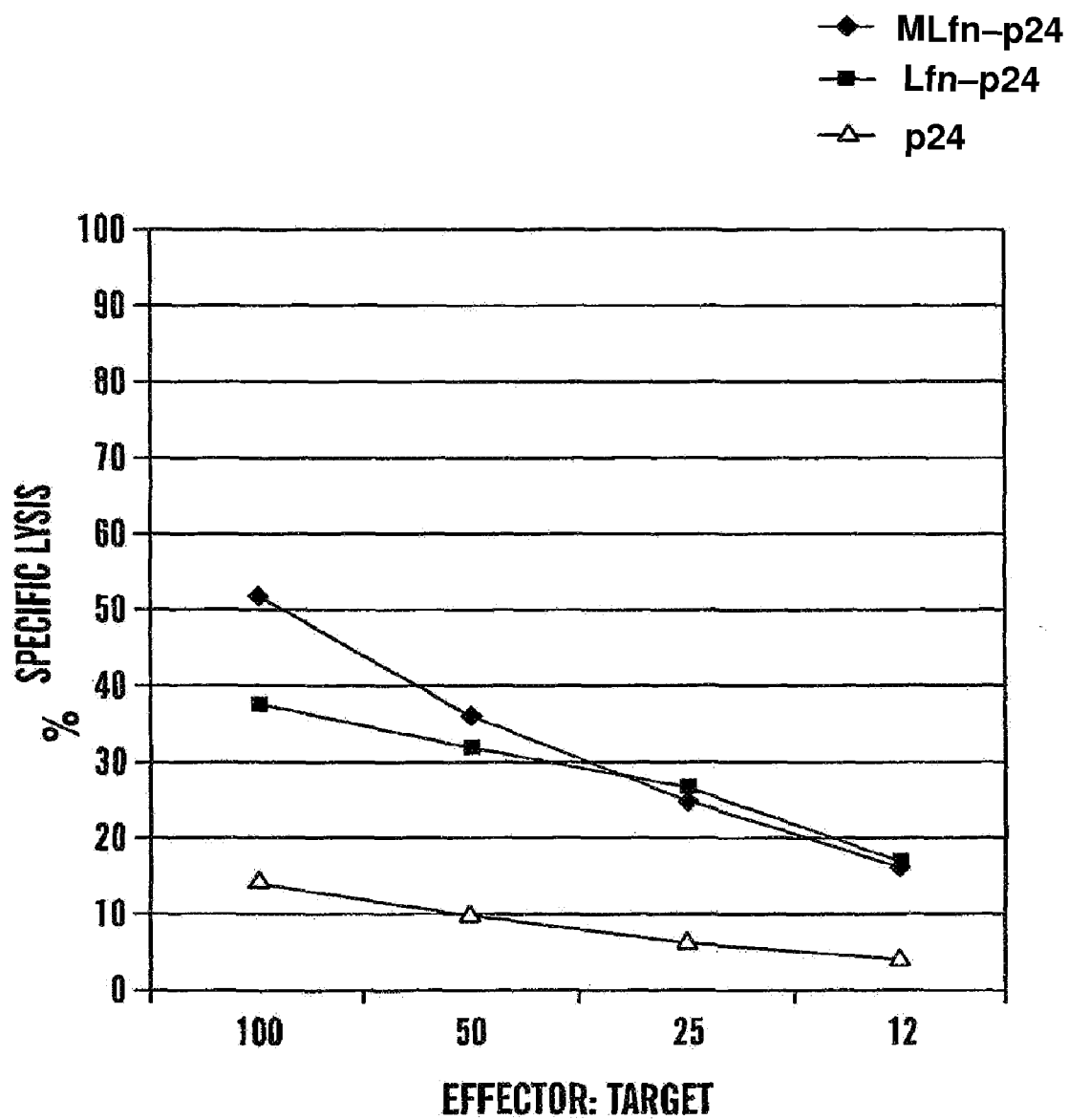
FIG. 18 Three groups of BALB/c mice, four in each group, were immunized i.p. with 15 ug LFn-p24, 15 ug MLFn-p24, and 15 ug p24, respectively. The CTL in splenic tissues were tested one after the immunization.

We then compared the CTL induction by LFn-p24 with MLFn-p24 in immunized mice. In FIG. 18, three groups of BALB/c mice, four in each group, were immunized i.p. with 15 μg LFn-p24, 15 μg MLFn-p24, and 15 μg p24, respectively. The CTL in splenic tissues were tested one after the immunization.

As shown in FIG. 18, both LFn-p24 and MLFn-p24 stimulated significant CTL activity after only one immunization. In fact, we repeatedly observed an improved CTL induction by MLFn-p24 compared to that induced by LFn-p24. This experiment also demonstrates that the C-terminal half of LFn (150-253) is indeed responsible for the intracellular antigen delivery, as the deletion of the MLFn sequence from the antigen (p24) abolishes the efficient CTL induction.

REFERENCES

1. Anderson, K. S., J. Alexander, M. Wei, and P. Cresswell 1993. Intracellular transport of class I MHC molecules in antigen processing mutant cell lines Journal of Immunology. 151:3407-19.
2. Androlewicz, M. J., K. S. Anderson, and P. Cresswell 1993. Evidence that transporters associated with antigen processing translocate a major histocompatibility complex class I-binding peptide into the endoplasmic reticulum in an ATP-dependent manner Proceedings of the National Academy of Sciences of the United States of America. 90:9130-4.
3. Ballard, J. D., A. M. Doling, K. Beauregard, R. J. Collier, and M. N. Starnbach 1998. Anthrax toxin-mediated delivery in vivo and in vitro of a cytotoxic T-lymphocyte epitope from ovalbumin Infection & Immunity. 66:615-9.
4. Borrow, P., H. Lewicki, B. H. Hahn, G. M. Shaw, and M. B. A. Oldstone 1994. Virus-specific CD8+ cytotoxic T-lymphocyte activity associated with control of viremia in primary human immunodeficiency virus type 1 infection J. Virol. 68:6103-6110.
5. Borrow, P., H. Lewicki, X. Wei, M. S. Horwitz, N. Peffer, H. Meyers, J. A. Nelson, J. E. Gairin, B. Hahn, M. B. Oldstone, and G. M. Shaw 1997. Antiviral pressure exerted by HIV-1-specific cytotoxic T lymphocytes (CTLs) during primary infection demonstrated by rapid selection of CTL escape virus Nature Medicine. 3:205-211.
6. Cao, H., P. Kanki, J.-L. Sankale, A. Dieng-Sarr, G. P. Mazzara, S. A. Kalams, B. Korber, S. MBoup, and B. D. Walker 1997. Cytotoxic T-lymphocyte cross-reactivity among different human immunodeficiency virus type 1 clades: implication for vaccine development J. Virol. 71:8615-23.
7. Cao, H., I. Mani, R. Vincent, R. Mugerwa, P. Mugyenyi, P. Kanki, J. Ellner, and B. D. Walker 2000. Cellular immunity to HIV-1 Clades: relevance to HIV-1 vaccine trials in Uganda J. Infec Dis. 182:1350-56.
8. Doling, A. M., J. D. Ballard, H. Shen, K. M. Krishna, R. Ahmed, R. J. Collier, and M. N. Starnbach 1999. Cytotoxic T-lymphocyte epitopes fused to anthrax toxin induce protective antiviral immunity Infection & Immunity. 67:3290-6.
9. Falk, K., O. Rötzchke, K. Deres, J. Metzger, G. Jung, and H.-G. Rammensee 1991. Identification of naturally processed viral nonapeptides allows their quantification in infected cells and suggests an allele-specific T cell epitope forecast. J. Exp. Med. 174:425-434.
10. Finbloom, D. S., J. Martin, and R. K. Gordon 1987. Endocytosis of particulate and soluble IgG immune complexes: differential effects of cytoskeletal modulating agents Clinical & Experimental Immunology. 67:205-10.
11. Geisow, M. J., P. D'Arcy Hart, and M. R. Young 1981. Temporal changes of lysosome and phagosome pH during phagolysosome formation in macrophages: studies by fluorescence spectroscopy Journal of Cell Biology. 89:645-52.
12. Goldberg, A. L., and K. L. Rock 1992. Proteolysis, proteasomes and antigen presentation Nature. 357:375-9.
13. Hanna, P. C., D. Acosta, and R. J. Collier 1993. On the role of macrophages in anthrax Proceedings of the National Academy of Sciences of the United States of America. 90:10198-201.
14. Harding, C. V., and R. Song 1994. Phagocytic processing of exogenous particulate antigens by macrophages for presentation by class I MHC molecules Journal of Immunology. 153:4925-33.
15. Howard, J. C. 1995. Supply and transport of peptides presented by class I MHC molecules Current Opinion in Immunology. 7:69-76.
16. Klaus, G. G. 1973. Cytochalasin B. Dissociation of pinocytosis and phagocytosis by peritoneal macrophages Experimental Eye Research. 79:73-8.
17. Koup, R. A., J. T. Safrit, Y. Cao, C. A. Andrews, G. McLeod, W. Borkowsky, C. Farthing, and D. D. Ho 1994. Temporal association of cellular immune responses with the initial control of viremia in primary human immunodeficiency virus type 1 syndrome J. Virol. 68:4650-4655.
18. Lalvani, A., R. Brookes, S. Hambleton, W. J. Britton, A. V. Hill, and A. J. McMichael 1997. Rapid effector function in CD8+ memory T cells Journal of Experimental Medicine. 186:859-65.
19. Lu, Y., R. Friedman, N. Kushner, A. Doling, L. Thomas, N. Touzjian, M. Starnbach, and J. Lieberman 2000. Genetically modified anthrax lethal toxin safely delivers whole HIV protein antigens into the cytosol to induce T cell immunity Proceedings of the National Academy of Sciences of the United States of America. 97:8027-32.
20. Man, S., R. D. Salter, and V. H. Engelhard 1992. Role of endogenous peptide in human alloreactive cytotoxic T cell responses International Immunology. 4:367-75.
21. Neefjes, J., F. Momberg, and G. Hammerling 1993. Selective and ATP-dependent translocation of peptides by the MHC-encoded transporter. Science. 261:769-771.
22. Ogg, G. S., X. Jin, S. Bonhoeffer, P. R. Dunbar, M. A. Nowak, S. Monard, J. P. Segal, Y. Cao, S. L. Rowland-Jones, v. Cerundolo, A. Hurley, M. Markowitz, D. D. Ho, D. F. Nixon, and A. J. McMichael 1998. Quantitation of HIV-1-specific cytotoxic T lymphocytes and plasma load of viral RNA Science. 279:2103-6.
23. Ohkuma, S., and B. Poole 1978. Fluorescence probe measurement of the intralysosomal pH in living cells and the perturbation of pH by various agents Proceedings of the National Academy of Sciences of the United States of America. 75:3327-31.
24. Ortmann, B., M. J. Androlewicz, and P. Cresswell 1994. MHC class I/beta 2-microglobulin complexes associate with TAP transporters before peptide binding Nature. 368: 864-7.
25. Pfeifer, J. D., M. J. Wick, R. L. Roberts, K. Findlay, S. J. Normark, and C. V. Harding 1993. Phagocytic processing of bacterial antigens for class I MHC presentation to T cells Nature. 361:359-62.
26. Pinto, L. A., J. Sullivan, J. A. Berzofsky, M. Clerici, H. A. Kessler, A. L. Landay, and G. M. Shearer 1995. ENV-specific cytotoxic T lymphocyte responses in HIV seronegative health care workers occupationally exposed to HIV-contaminated body fluids J. Clin. Invest. 96:867-76.
27. Powis, S. J. 1997. Major histocompatibility complex class I molecules interact with both subunits of the transporter associated with antigen processing, TAP1 and TAP2 European Journal of Immunology. 27:2744-7.
28. Rowland-Jones, S., J. Sutton, K. Ariyoshi, T. Dong, F. Gotch, S. McAdam, D. Whitby, S. Sabally, A. Gallimore, T. Corrah, M. Takiguchi, T. Schultz, A. McMichael, and H. Whittle 1994. Resistance to HIV-1 infection-HIV-specific cytotoxic T lymphocytes in HIV-exposed but uninfected Gambian women Nature Medicine. in Press.
29. Sadasivan, B., P. J. Lehner, B. Ortmann, T. Spies, and P. Cresswell 1996. Roles for calreticulin and a novel glycoprotein, tapasin, in the interaction of MHC class I molecules with TAP Immunity. 5:103-14.
30. Solheim, J. C., M. R. Harris, C. S. Kindle, and T. H. Hansen 1997. Prominence of beta 2-microglobulin, class I heavy chain conformation, and tapasin in the interactions of class I heavy chain with calreticulin and the transporter associated with antigen processing Journal of Immunology. 158:2236-41.
31. Song, R., and C. V. Harding 1996. Roles of proteasomes, transporter for antigen presentation (TAP), and beta 2-microglobulin in the processing of bacterial or particulate antigens via an alternate class I MHC processing pathway Journal of Immunology. 156:4182-90.
32. Suh, W. K., M. F. Cohen-Doyle, K. Fruh, K. Wang, P. A. Peterson, and D. B. Williams 1994. Interaction of MHC class I molecules with the transporter associated with antigen processing Science. 264:1322-6.
33. Wei, M. L., and P. Cresswell 1992. HLA-A2 molecules in an antigen-processing mutant cell contain signal sequence-derived peptides. Nature. 356:443-6.
34. Yewdell, J. W., and J. R. Bennink 1989. Brefeldin A specifically inhibits presentation of protein antigens to cytotoxic T lymphocytes Science. 244:1072-5.

All references described herein are incorporated herein by reference.

What is claimed:

1. A method for measuring a cell mediated immune response, comprising contacting a cell with an isolated polypeptide comprising a target antigen and a transport factor, wherein the transport factor contains a fragment of at least 104 C-terminal amino acids of a bipartate protein exotoxin which is not toxic to the cell and functions to deliver the target antigen to the cytosol of the cell, and wherein a protective antigen (PA) of a bipartate exotoxin is not present, and measuring the increase in at least one cytokine or the increase in a cell surface antigen expressed on the cell in response to delivering the target antigen to the cytosol of the cell, wherein the increase of at least one cytokine or expression of a cell surface antigen by the cell, as compared to the corresponding at least one cytokine or expression of a cell surface antigen in the absence of the target antigen and transport factor, is indicative of a cell mediated immune response.

2. A method for measuring a cell mediated immune response in vitro, comprising contacting a cell with a polypeptide comprising a target antigen linked to transport factor from B. anthracia, wherein the transport factor is a bipartate protein exotoxin that is not toxic to the cell, and wherein the protective antigen (PA) of the bipartate exotoxin is not present, and measuring the increase in at least one cytokine or the increase in a cell surface antigen expressed on the cell in response to delivering the target antigen to the cytosol of the cell, wherein the increase in at least one cytokine or expression of a cell surface antigen by the cell, as compared to the corresponding at least one cytokine or expression of a cell surface antigen in the absence of the target antigen linked to the transport factor, is indicative of a cell mediated immune response.

3. The method of claim 1 or 2, wherein the transport factor comprises at least residues 185-288 of SEQ ID NO: 2.

4. The method of claim 1 or 2, wherein the transport factor comprises at least residues 35-288 of SEQ ID NO: 2.

5. The method of claim 2, wherein the polypeptide is a bacterial target antigen.

6. The method of claim 5, wherein the bacterial target antigen is a polypeptide from S. typhi or Mycobacteria.

7. The method of claim 6, wherein the Mycobacteria is M. tuberculosis.

8. A kit for measuring a cell mediated immune response in vitro comprising a cocktail of different polypeptides, wherein each polypeptide is a target antigen which is bound to a transport factor, wherein the transport factor comprises at least residues 185-288 of SEQ ID NO: 2 and wherein the protective antigen (PA) of B. anthracis bipartate exotoxin is not present.

9. The kit of claim 8, wherein the transport factor comprises at least residues 34-288 of SEQ ID NO: 2.

10. The kit of claim 8, wherein at least one polypeptide comprises a target antigen which is a bacterial target antigen.

11. The kit of claim 10, wherein the bacterial target antigen is a polypeptide from S. typhi or Mycobacteria.

12. The kit of claim 11, wherein the Mycobacteria is M. tuberculosis.

13. The method of claim 1 or 2, wherein the cytokine is selected from the group consisting of: interferon, IL-2, IL-12, IL-4, GM-CSF, CpG.

14. The method of claim 13, wherein the interferon is INF-γ.

15. The method of claim 1 or 2, wherein the cell-surface marker is expressed by a T-cell.

16. The method of claim 15, wherein the cell-surface marker expressed by a T-cell is selected from the group consisting of: CD96, CD8, CD3.

17. The method of claim 1 or 2, wherein the cytokine is measured by any one of: ELISA assay, ElisSPOT assay or flow-based intracellular cytokine assay.

18. The method of claim 1 or 2, wherein the cell is an immune cell.

19. The method of claim 18, wherein the immune cell is selected from PBMCs, T-cell.

* * * * *